(12) United States Patent
Siddiqui et al.

(10) Patent No.: US 9,248,169 B2
(45) Date of Patent: Feb. 2, 2016

(54) SCHISTOSOMIASIS VACCINE COMPOSITIONS AND METHODS OF USE

(75) Inventors: Afzal A. Siddiqui, Wolfforth, TX (US);
Gul Ahmad, Lubbock, TX (US);
Weidong Zhang, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 12/821,544

(22) Filed: Jun. 23, 2010

(65) Prior Publication Data

US 2011/0091507 A1    Apr. 21, 2011

Related U.S. Application Data

(60) Provisional application No. 61/219,382, filed on Jun. 23, 2009.

(51) Int. Cl.
*A61K 39/00* (2006.01)
*C07K 14/435* (2006.01)
*C12N 9/64* (2006.01)

(52) U.S. Cl.
CPC ....... *A61K 39/0003* (2013.01); *C07K 14/43559* (2013.01); *C12N 9/6402* (2013.01); *C12Y 304/22052* (2013.01); *A61K 2039/53* (2013.01); *A61K 2039/545* (2013.01); *A61K 2039/55511* (2013.01); *A61K 2039/55561* (2013.01)

(58) Field of Classification Search
CPC ........... A61K 39/0003; A61K 2039/53; A61K 39/545; A61K 39/55561; C07K 14/43559
USPC ...................... 424/265.1; 435/320.1; 536/23.1
See application file for complete search history.

(56) References Cited

PUBLICATIONS

Hota-Mitchell et al, Vaccine 15(15):1631-1640, 1997.*
Siddiqui et al, Vaccine 21:2882-2889, 2003.*
Siles-Lucas et al, Vaccine 25:7217-7223, 2007.*
Chiaramonte et al, J. Immunol. 164:973-985, 2000.*
Zhu et al, Southeast Asian J. Trop. Med. Public Health 33(2):207-213, 2002; Abstract only.*
Gryseels B, et al. "Human schistosomiasis" Lancet 2006;368(September (9541)): 1106-18.
Steinmann P, et al.,"Schistosomiasis and water resources development: systematic review, meta-analysis, and estimates of people at risk" Lancet Infect Dis 2006;6(Jul. (7)):411-25.
Bergquist R, et al. "Blueprint for schistosomiasis vaccine development" Acta Trop 2002;82(May (2)):183-92.
Siddiqui AA, et al. "Experimental vaccines in animal models for schistosomiasis" Parasitol Res 2008;102(Apr. (5)):825-33.
McManus DP, et al. "Current status of vaccines for schistosomiasis" Clin Microbial Rev 2008;21(Jan. (1)):225-42.
Siddiqui AA, et al. "Characterization of Ca(2+ )-dependent neutral protease ( calpain) from human blood flukes, Schistosoma manson" Biochim Biophys Acta 1993;1181(Mar. (1)):37-44.

Young BW, et al. "Complement and 5-HT increase phosphatidylcholine incorporation into the outer bilayers of Schistosoma mansoni" J Parasitol1986;72(Oct. (5)):802-3.
Van Hellemond JJ, et al. "Functions of the tegument of schistosomes: clues from the proteome and lipidome" Int J Parasitol 2006;36(May (6)):691-9.
Ahmad G, et al. "Protective and antifecundity effects of Sm-p80-based DNA vaccine formulation against Schistosoma mansoni in a nonhuman primate model" Vaccine 27 (2009): 2830-2837.
Hota-Mitchell S, et al. "Recombinant vaccinia viruses and gene gun vectors expressing the large subunit of Schistosoma mansoni calpain used in a murine immunization-challenge model" Vaccine 1999;17(Mar. (11-12)):1338-54. [Abstract].
Siddiqui AA, et al. "Characterization of protective immunity induced against Schistosoma mansoni via DNA priming with the large subunit of calpain (Sm-p80) in the presence of genetic adjuvants" Parasite 2005;12(Mar. (1)):3-8.
Jankovic D, et al. "Calpain is the target antigen of a Th1 clone that transfers protective immunity against Schistosoma manson" J Immunol1996;157(Jul. (2)):806-14. [Abstract].
Ohta N, et al. "Research on calpain of Schistosomajaponicum as a vaccine candidate" Parasitol Int 2004;53(Jun. (2)):175-81.
Ridi RE, et al. "Schistosoma mansoni ex vivo lung-stage larvae excretory-secretory antigens as vaccine candidates against schistosomiasis" Vaccine 2009;27(5):666-73.
Zhang R, et al. "Vaccination with calpain induces a Th1-biased protective immune response against Schistosoma japonicum" Infect Immun 2001;69(Jan. (1)):386-91.
Kennedy RC, et al. "Nonhuman primate models to evaluate vaccine safety and immunogenicity" Vaccine 1997;15(Jun. (8)):903-8.
Siddiqui AA, et al. "Induction of protective immunity against Schistosoma mansoni via DNA priming and boosting with the large subunit of calpain (Sm-p80): adjuvant effects of granulocyte-macrophage colonystimulating factor and interleukin-4" Infect Immun 2003;71(Jul. (7)):3844-51.
Siddiqui AA, et al. "Characterization of the immune response to DNA vaccination strategies for schistosomiasis candidate antigen, Sm-p80 in the baboon" Vaccine 2005;23(Feb. (12)):1451-6.
Cheever A W. "Conditions affecting the accuracy of potassium hydroxide digestion techniques for counting Schistosoma mansoni eggs in tissues" Bull World Health Organ 1968;39(2):328-31.

(Continued)

*Primary Examiner* — Kevin Hill
(74) *Attorney, Agent, or Firm* — Edwin S. Flores; Chainey P. Singleton; Chalker Flores, LLP

(57) ABSTRACT

No effective vaccine exists for the devastating parasitic disease of Schistosomiasis. The present invention focuses on Sm-p80, a functionally important antigen of *Schistosoma mansoni* that plays a pivotal role in the schistosome immune evasion process. When used in a novel vaccine formulation, Sm-p80 demonstrates consistent immunogenicity, protective potential, and antifecundity effects. Two novel DNA constructs were made for immunization purposes. Sm-p80 coding sequence was cloned into VR 1020. Additionally, Sm-p80 coding sequence was cloned into pcDNA3.1 with flanking CpG motifs on each end of the Sm-p80 sequence. When used in different vaccine formulations, both of the constructs demonstrate the superior antifecundity and anti-worm effects of Sm-p80, which has great potential as an important vaccine candidate for the reduction of the morbidity associated with schistosome infection.

12 Claims, 17 Drawing Sheets

(56) References Cited

PUBLICATIONS

Shearer MH, et al. "Comparison and characterization of immunoglobulin G subclasses among primate species" Clin Diagn Lab Immunol 1999;6(Nov. (6)):953-8.

Vereecken K, et al. "Associations between specific antibody responses and resistance to reinfection in a Senegalese population recently exposed to Schistosoma mansoni" TropMed Int Health 2007;12(Mar. (3)):431-44.

Acosta LP, et al. "Immune correlate study on human Schistosomajaponicum in a well-defined population in Leyte, Philippines. II. Cellular immune responses to S. japonicum recombinant and native antigens" Acta Trop 2002;84 (Nov. (2)):137-49. [Abstract].

Olds GR. "New insights into the observed age-specific resistance to reinfection with Schistosomajaponicum" Clin Infect Dis 2006;42(Jun. (12)):1699-701.

Hewitson JP, et al. "Immunity induced by the radiation-attenuated schistosome vaccine" Parasite Immunol2005;27(Jul. (7-8)):271-80.

Lightowlers MW. "Cestode vaccines: origins, current status and future prospects" Parasitology 2006;133(Suppl.):S27-42.

Vercruysse J, et al. "Control of parasitic disease using vaccines: an answer to drug resistance?" Rev Sci Tech 2007;26 (Apr. (1)):105-15. [Abstract].

Kumagai T, et al. "Schistosoma japonicum: localization of calpain in the penetration glands and secretions of cercariae" Exp Parasitol2005;109(Jan. (1)):53-7.

Damian RT, et al "Further development of the baboon as a model for acute schistosomiasis" Mem Inst Oswaldo Cruz 1992;87(Suppl. 4):261-9.

Nyindo M, et al. "The baboon as a non-human primate model of human schistosome infection" Parasitol Today 1999;15(Dec. (12)):478-82.

Boulanger D, et al. "Immunization of mice and baboons with the recombinant Sm28GST affects both worm viability and fecundity after experimental infection with Schistosoma manson" Parasite Immunol1991;13(Sep. (5)): 473-90. [Abstract].

Kanamura HY, et al. "Schistosoma mansoni heat shock protein 70 elicits an early humoral immune response inS. mansoni infected baboons" Mem Inst Oswaldo Cruz 2002;97(Jul. (5)):711-6.

Kariuki TM, et al. "Parameters of the attenuated schistosome vaccine evaluated in the olive baboon" Infect Immun 2004;72(Sep. (9)):5526-9.

Reid GD, et al. "Schistosoma haematobium in the baboon (*Papio anubis*): assessment of protection levels against either a single mass challenge or repeated trickle challenges after vaccination with irradiated schistosomula" J Helminthol 1995;69(Jun. (2)):139-47. [Abstract].

Soisson LA, et al. "Protective immunity in baboons vaccinated with a recombinant antigen or radiationattenuated cercariae ofSchistosomamansoni is antibody-dependent" J Immunol1993;151(Nov. (9)):4782-9.

Yole DS, et al. "Protective immunity to Schistosoma mansoni induced in the olive baboon Papio anubis by the irradiated cercaria vaccine" Parasitology 1996;112(Jan. (Pt 1)):37-46. [Abstract].

Kariuki TM, et al. "Resistance to re-infection after exposure to normal and attenuated schistosome parasites in the baboon model" Parasite Immunol2005;27(Jul. (7-8)):281-8.

Stacy S, et al. "An ageold paradigm challenged: old baboons generate vigorous humoral immune responses to LcrV, a plague antigen" J Immunol2008;181(Jul. (1)):109-15.

Coulson PS, et al. "Schistosome vaccine testing: lessons from the baboon model" Mem Inst Oswaldo Cruz 2006;101(September (Suppl. 1)): 369-72.

Wilson RA, et al. "Elimination of Schistosoma mansoni adult worms by rhesus macaques: basis for a therapeutic vaccine?" PLoS Negl Trop Dis 2008;2(9):e290.

* cited by examiner

SCHISTOSOMIASIS VACCINE COMPOSITIONS AND METHODS OF USE

CROSS-REFERENCE TO RELATED APPLICATIONS

This application claims the benefit under Title 35 United States Code §119(e) of U.S. Provisional Patent Application Ser. No. 61/219,382; Filed: Jun. 23, 2009, the full disclosure of which is incorporated herein by reference.

STATEMENT REGARDING FEDERALLY SPONSORED RESEARCH OR DEVELOPMENT

This application was supported by grants from the National Institute of Allergy and Infectious Diseases, NIH, Grant Number R01AI071223, entitled "Experimental Molecular Vaccines for Schistosomiasis" and Grant Number R15 AI50534-01, entitled "Schistosome Calpain as a Vaccine Candidate." The government may have certain rights to the invention.

THE NAMES OF THE PARTIES TO A JOINT RESEARCH AGREEMENT

Not applicable

INCORPORATING-BY-REFERENCE OF MATERIAL SUBMITTED ON A COMPACT DISC

Not applicable

SEQUENCE LISTING

Not applicable

FIELD OF THE INVENTION

The present invention relates to DNA and protein vaccine formulations against *Schistosoma mansoni*. More specifically, the present invention relates to compositions and methods for use for controlling the human parasitic disease, schistosomiasis.

BACKGROUND OF THE INVENTION

Without limiting the scope of the disclosed compositions and methods, the background is described in connection with a novel Sm-p80-based vaccine formulation against *Schistosoma mansoni*.

*Schistosoma mansoni* is a flatworm parasite that inhabits the porto-mesenteric circulation of humans. Considerable morbidity and mortality results from the affliction of an estimated 207 million people worldwide by several species of schistosomes. An additional 779 million people are at risk of acquiring this infection. Disability-adjusted life years for schistosomiasis have been calculated to be somewhere between 1.7 million and 4.5 million years. Schistosomiasis is endemic in 74 developing countries.

The infective cycle of *Schistosoma mansoni* involves asexual reproduction within an intermediate snail host, followed by infection of a human host. Cercariae, the larval stage which exits from an intermediate snail host, infect humans by penetrating human skin. These juvenile schistosomes mature to schistosomula, undergo an intricate migration through the host's lungs and liver, and develop into sexually mature egg-laying adults. Sexually mature male and female schistosomes begin the egg-laying phase of the life cycle within the intestinal venules. The constant production of large numbers of ova results in the excretion of some eggs with fecal matter, and in heavy infection, entrapment of eggs in visceral organs with ensuing host granulomatous immune responses directed against them. It is this egg-induced organ damage which results in complications such as hepatic fibrosis, portal hypertension, and esophageal varices, which lead to the death of chronically infected hosts.

The chronic nature of this debilitating disease results in cumulative damage to the liver, spleen, and colon due to the granulomatous reaction to accumulated embryonated eggs. Infection results in the production of circulating anti-schistosomal antibodies. The immune response is erratic, however, and does not lead to sterile immunity. Additionally, the adult parasites evade immune clearance by complex and multifactorial mechanisms.

Emphasis has been placed on chemotherapy as the preferred method for the treatment of schistosomiasis. Control programs based on chemotherapy are complicated, however, by the rapidity and frequency of re-infection and the difficulties and expense involved in maintaining these programs over a long term. The continuous drug treatment and re-infection cycle fails to reduce the overall egg output sufficiently to markedly reduce transmission of the disease in endemic areas. Additionally, concerns exist that the parasites may develop drug resistance. A critical need remains for the development of alternate approaches to control the disease.

No effective vaccine exists for schistosomiasis. Even though anti-parasitic drugs and other control measures, including public hygiene and snail control are available, the advent of an effective vaccine still remains the most potentially powerful means for the control of this disease. Vaccination of individuals at a young age would be the most efficient way of priming the immune system without the accompaniment of egg-induced pathology. A vaccine would also prevent severe infection and thus decrease transmission of eggs and help curb the cycle of *S. mansoni* infection. Boosting of immunity to schistosomes in vaccinated individuals would occur following subsequent exposure to infective cercariae.

Several adult *S. mansoni* proteins have been considered as potential vaccine candidates. Ideally, the most promising vaccine candidates may be those which are surface-exposed and are indispensable for the parasite's survival within the human host.

A major problem that has hindered schistosomiasis vaccine research and development concerns the identification and selection of potential protective antigens encoded by the parasite. During the last two decades, many laboratories have attempted to identify schistosomal antigens that induce partially protective immune responses. More than 100 such antigens have been identified, about 25% of which confer protection of varying degrees. None of these candidate antigens, however, have induced levels of an immune response approaching immunity levels (~80%) that have been observed following vaccination with irradiated schistosome larvae. Independent examination of the six "priority antigens" (paramyosin, glutathione S-transferase, fatty acid binding 14 kDa protein, IrV-5, triose phosphate isomerase, and Sm23) via a standard comparative World Health Organization delineated procedure, resulted in none of the antigens providing the stated goal of 40% protection or better.

Schistosomes interact closely with their host, performing functions such as immune evasion, nutrient uptake, and attachment. Host-exposed schistosome proteins that undertake such essential functions are effective targets for a schistosomiasis vaccine. One such protein is the large subunit of calpain (Sm-p80) which plays an important role in the surface membrane renewal of schistosomes, an immune evasion mechanism employed by blood-dwelling helminths to evade host immunity. Sm-p80 is exposed at the host parasite interface and is naturally immunogenic. While the natural immunogenicity of the molecule does not provide protection under conditions of natural infection, it is possible to present calpain to the immune system in such a way as to induce potent immunity. The UNDP/World Bank/WHO-TDR special panel designated Sm-p80 as one of the priority antigens "with established credentials, needing further development" and Sm-p80 is now considered as one of the "first-tier candidates" by international experts in the field.

An efficacious schistosomiasis vaccine would make a significant contribution to current schemes of disease control, particularly if it provides a potent, long-lasting immunity to the disease. Such a vaccine would greatly reduce the need for logistically difficult and expensive drug-based programs which often require political commitment and well-funded public health systems. Even partial protection against cercarial infection would be a significant advance because a vaccine that reduces worm burden will reduce both the pathology and the transmission rates of the disease. This is because schistosomes, unlike most other infectious organisms, do not replicate within their definitive hosts. Therefore, a sterilizing immunity may not be required for schistosomiasis. The Scientific Working Group on schistosomiasis at the World Health Organization (WHO) has determined that vaccines that lower adult worm burdens by 50% will be effective in reducing overall morbidity and mortality.

Most schistosome vaccine candidates confer 30-50% protection in the mouse model system. Thus, there is a great need to identify novel antigens, adjuvant vehicles, and cocktail vaccine formulations to induce protection that ranges from 70% to 80%, as has been recorded with radiation-attenuated vaccines.

The present invention proposes a novel vaccine formulation based on a schistosome protein, calpain, which was originally determined to be involved in schistosome surface membrane biogenesis. Calpain has two subunits, the larger of which, Sm-p80, has shown great potential as a relevant vaccine antigen for reduction of the morbidity associated with both *Schistosoma mansoni* and *Schistosoma japonicum*.

BRIEF SUMMARY OF THE INVENTION

The present invention, therefore, provides compositions and methods for use for controlling the human parasitic disease, schistosomiasis. The vaccine is comprised of various formulations and delivery methods for Sm-p80, a schistosome protein. This is the first effective vaccine formulation against *Schistosoma mansoni*. Current control strategies, including integrated control programs aimed at limiting schistosomiasis by improving education and sanitation, molluscicide treatment programs to reduce the population of the intermediate snail host, and chemotherapy, have had only limited success. Thus, there remains a critical need for the development of alternate approaches to control the disease, for example a vaccine.

In summary, the present invention discloses compositions and methods for use of a novel Sm-p80-based DNA vaccine formulation against *S. mansoni*.

BRIEF DESCRIPTION OF THE SEVERAL VIEWS OF THE DRAWINGS

For a more complete understanding of the features and advantages of the present invention, reference is now made to the detailed description of the invention along with the accompanying figures in which.

DETAILED DESCRIPTION OF THE INVENTION

Disclosed herein are compositions and methods for use of a Sm-p80-based vaccine formulation against *Schistosoma mansoni*. The numerous innovative teachings of the present invention will be described with particular reference to several embodiments (by way of example, and not of limitation).

Figure 1:
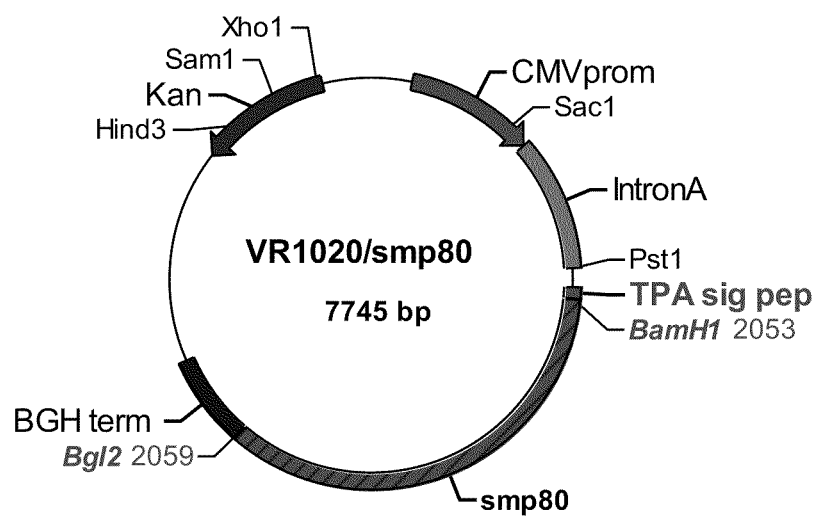
FIG. 1 is a depiction of the DNA construct in which the Sm-p80 coding sequence is cloned into VR 1020 and thus one of the DNA vaccine formulations in accordance with embodiments of the disclosure.

Reference is first made to FIG. 1, a schematic of the VR1020/Sm-p80 construct. FIG. 1, the first of two constructs, depicts a DNA construct created by cloning schistosome Sm-p80 coding sequence into VR1020.

Figure 2:
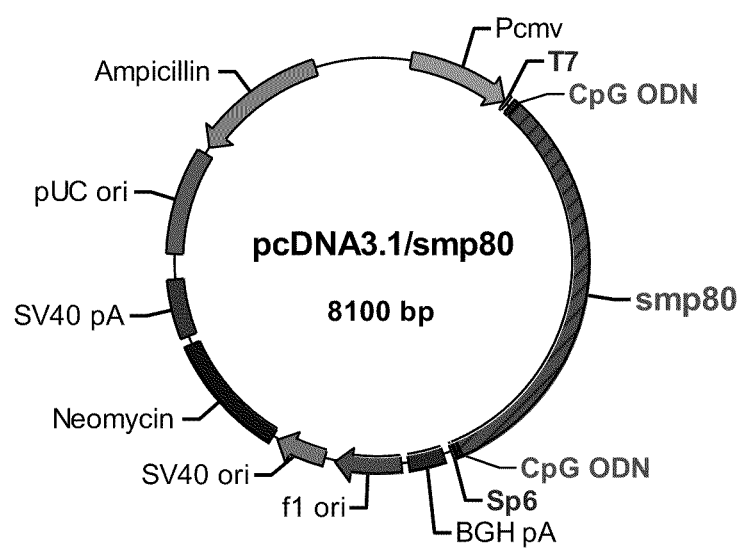
FIG. 2 is a depiction of the DNA construct in which the Sm-p80 coding sequence is cloned into pcDNA 3.1 with flanking CpG motifs on each end of the Sm-p80 sequence constituting another DNA vaccine formulation in accordance with embodiments of the disclosure.

Reference is now made to FIG. 2, a schematic of the pcDNA3.1/Sm-p80 construct. FIG. 2, the second of two constructs, depicts a DNA construct created by cloning schistosome Sm-p80 coding sequence into pcDNA 3.1 with flanking CpG motifs on each end of the Sm-p80 sequence. One having ordinary skill in the art will be able to construct the DNA vaccine relying on FIG. 2.

Figure 3:
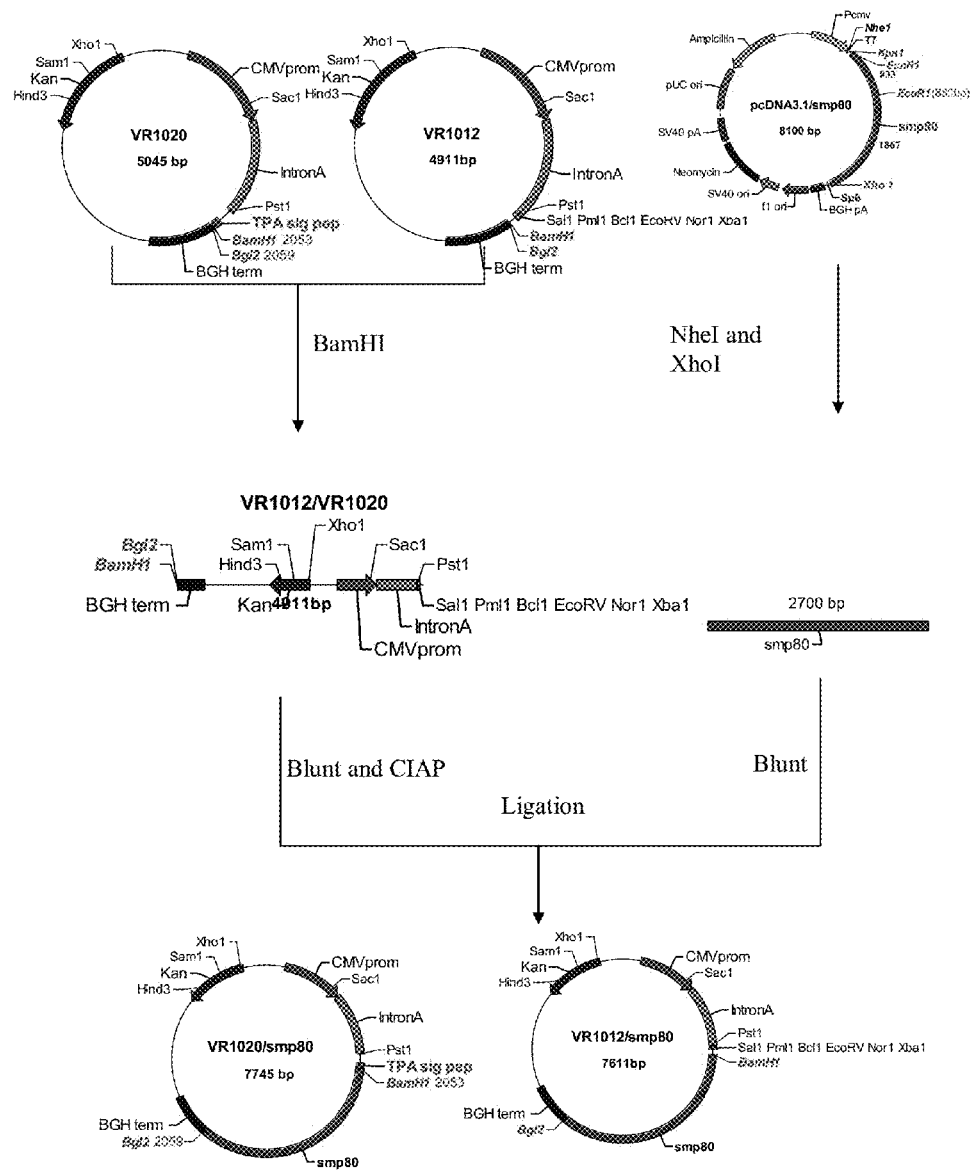
FIG. 3 is a depiction of the first method of construction of VR1020/Sm-p80 and pcDNA3/Sm-p80 in accordance with embodiments of the disclosure.

Reference is now made to FIG. 3, a schematic diagram illustrating the first method of construction of VR1020/Sm-p80 and pcDNA3/Sm-p80.

Figure 4:
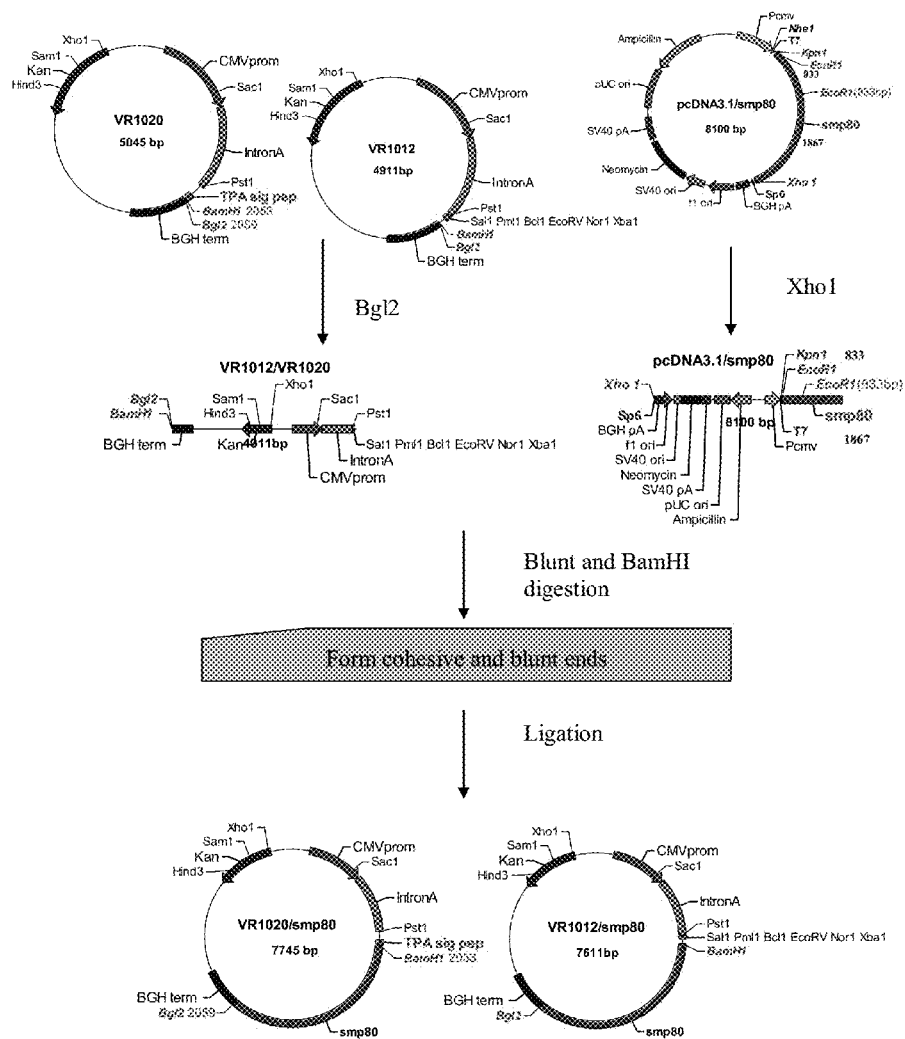
FIG. 4 is a depiction of the second method of construction of pcDNA3/Sm-p80 and VR1012/Sm-p80 in accordance with embodiments of the disclosure.

Reference is now made to FIG. 4, a schematic diagram illustrating the second method of construction of VR1020/Sm-p80 and pcDNA3/Sm-p80.

One having ordinary skill in the art will be able to construct the DNA vaccine relying on FIG. 1 in combination with FIG. 3 or FIG. 4.

Both of the constructs depicted in FIG. 1 and FIG. 2 were used in different vaccine formulations (DNA alone and prime boost) which were delivered to mice and baboons. This is first ever use of an Sm-p80-based vaccine formulation in the baboon model of schistosomiasis. Table 1 summarizes the 1. Sm-p80-based vaccine formulation [(a) DNA vaccine alone, (b) DNA vaccine in which two unmethylated CpG motifs are inserted in the construct because, they act as immunostimulants (c) recombinant Sm-p80 protein was introduced in presence of Oligodeoxynucleotides (ODN) containing CpG motifs activate host defense mechanisms leading to innate and acquired immune responses) 2. Vaccine delivery routes and 3. Results obtained. Experimental data on antifecundity and anti-worm effects of Sm-p80 in both murine and nonhuman primate models clearly indicate that this antigen has great potential as an important vaccine candidate for the reduction of the morbidity associated with schistosome infection. In summary, Sm-p80-based vaccine formulations have three protective effects (worm reduction, antifecundity effect and protection against acute schistosomiasis). This is a first report of an anti-schistosome defined vaccine formulation which has shown these three protective effects.

TABLE 1

| Vaccine Formulation | Delivery Method | Animal Model | % Worm Reduction | % Reduction in egg production |
|---|---|---|---|---|
| Sm-p80-VR1020 | Intramuscular injection with three boosts (DNA vaccine) | Mouse | 46% | Not tested |
| Sm-p80-VR1020 | Intramuscular injection with three boosts (DNA vaccine) | Baboon | 47% | 29% |
| Sm-p80-pcDNA3-2CpG | Intramuscular injection with three boosts (DNA vaccine) | Mouse | 60% | Not tested |

TABLE 1-continued

| Vaccine Formulation | Delivery Method | Animal Model | % Worm Reduction | % Reduction in egg production |
|---|---|---|---|---|
| Sm-p80-pcDNA3 + ODN | Priming with Sm-p80-pcDNA 3 followed by boosting with recombinant Sm-p80 in the presence of ODN (Prime/Boost vaccine) | Mouse | 58% | 69% |
| Sm-p80 recombinant protein + ODN | Primary vaccination and boosting was performed with recombinant Sm-p80 in the presence of ODN (Recombinant Protein Vaccine) | Mouse | 69% | 75% |

Table 2 and Table 3 detail the protocols used for immunization of mice with the pcDNA-based vector.

TABLE 2

Immunization regimen using Sm-p80 in CpG-enriched vectors plus Th1 enhancer cytokine(s) followed by boosting with recombinant Sm-p80 with CpG oligonucleotides as an adjuvant

| Groups of Mice (n = 15) | Primary Immunization (Wk-0) | First Boost (Wk-4) | Second Boost (Wk-8) |
|---|---|---|---|
| Control Group 1 | PBS alone | PBS alone | PBS alone |
| CpG | 100 µg ISS-ISS-pcDNA3 | 50 µg ODN # 2138 | 50 µg ODN # 2138 |
| CpG + Sm-p80 | 100 µg ISS-Sm-p80-ISS-pcDNA3 | 25 µg rSm-p80 with 50 µg ODN # 2006 | 25 µg rSm-p80 with 50 µg ODN # 2006 |
| Control Group2 and 3 | 100 µg pcDNA3/pVITRO1 | 50 µg ODN # 2138 | 50 µg ODN # 2138 (If required) |
| Control Group4 | 100 µg pVITR01-mIL-2-mIL-12 | 50 µg ODN # 2138 | 50 µg ODN # 2138 (If required) |
| Sm-p80-pcDNA3 + cytokine(s) | 100 µg ISS-Sm-p80-ISS-pcDNA3 plus 100 µg pVITRO1-mIL-2-mIL-12 | 25 µg rSm-p80 with 50 µg ODN # 2006 | 25 µg rSm-p80 with 50 µg ODN # 2006 |

TABLE 3

Immunization regimen using Sm-p80 in CpG-enriched vectors plus Th1 enhancer cytokine(s) followed by boosting with recombinant Sm-p80 with novel immunomodulator resiquimod (R848) as an adjuvant.

| Groups of Mice (n = 15) | Primary Immunization (Wk-0) | First Boost (Wk-4) | Second Boost (Wk-8) |
|---|---|---|---|
| Control Group 1 | PBS alone | PBS alone | PBS alone |
| Control Group 2 and 3 | 100 µg pcDNA3/pVITRO1 | 10 µg resiquimod | 10 µg resiquimod |
| Experimental Group 1 | 100 µg Sm-p80-pcDNA3 | 10 µg resiquimod + 25 µg rSm-p80 | 10 µg resiquimod + 25 µg rSm-p80 |
| Experimental Group 2 | 100 µg ISS-Sm-p80-ISS-pcDNA3 | 10 µg resiquimod + 25 µg rSm-p80 | 10 µg resiquimod + 25 µg rSm-p80 |
| Control Group 4 | 100 µg pVITRO1-mIL-2-mIL-12 | 10 µg resiquimod | 10 µg resiquimod |
| Experimental Group 3 | 100 µg ISS-Sm-p80-ISS-pcDNA3 + 100 µg pVITRO1-mIL-2-mIL-12 | 10 µg resiquimod + 25 µg rSm-p80 | 10 µg resiquimod + 25 µg rSm-p80 |

Table 4 and Table 5 detail protocols used for the immunization of mice with the VR1020-based vector.

TABLE 4

Proposed Immunization regimen using CpG oligonucleotides (ODNs) as an adjuvant

| Groups of Mice (n = 15) | Primary Immunization (Wk-0) | First Boost (Wk-4) | Second Boost (Wk-8) |
|---|---|---|---|
| Control Group 1 | PBS alone | PBS alone | PBS alone |
| CpG | 100 µg ISS-ISS-VR1020 | 50 µg ODN # 2138 | 50 µg ODN # 2138 |
| CpG + Sm-p80 | 100 µg ISS-Sm-p80-ISS-VR1020 | 25 µg rSm-p80 with 50 µg ODN # 2006 | 25 µg rSm-p80 with 50 µg ODN # 2006 |
| Control Group2 and 3 | 100 µg VR1020/pVITRO1 | 50 µg ODN # 2138 | 50 µg ODN # 2138 (If required) |
| Control Group4 | 100 µg pVITRO1-mIL-2-mIL-12 | 50 µg ODN # 2138 | 50 µg ODN # 2138 (If required) |
| Sm-p80-pcDNA3 + cytokine(s) | 100 µg ISS-Sm-p80-ISS-VR1020 plus 100 µg pVITRO1-mIL-2-mIL-12 | 25 µg rSm-p80 with 50 µg ODN # 2006 | 25 µg rSm-p80 with 50 µg ODN # 2006 |

TABLE 5

Proposed Immunization regimen using resiquimod (R848) as an adjuvant

| Groups of Mice (n = 15) | Primary Immunization (Wk-0) | First Boost (Wk-4) | Second Boost (Wk-8) (if required) |
|---|---|---|---|
| Control Group 1 | PBS alone | PBS alone | PBS alone |
| Control Group 2 and 3 | 100 µg VR1020/pVITRO1 | 10 µg resiquimod | 10 µg resiquimod |
| Experimental Group 1 | 100 µg Sm-p80-VR1020 | 10 µg resiquimod + 25 µg rSm-p80 | 10 µg resiquimod + 25 µg rSm-p80 |
| Experimental Group 2 | 100 µg ISS-Sm-p80-ISS-VR1020 | 10 µg resiquimod + 25 µg rSm-p80 | 10 µg resiquimod + 25 µg rSm-p80 |
| Control Group 4 | 100 µg pVITRO1-mIL-2-mIL-12 | 10 µg resiquimod | 10 µg resiquimod |
| Experimental Group 3 | 100 µg ISS-Sm-p80-ISS-VR1020 + 100 µg pVITRO1-mIL-2-mIL-12 | 10 µg resiquimod + 25 µg rSm-p80 | 10 µg resiquimod + 25 µg rSm-p80 |

The protocols used for immunization of baboons included both naked DNA vaccination and prime boost and protein vaccination strategies. Protocols using naked DNA vaccination in baboons were as follows:

Group 1: For this control group, the initial immunization was with 500 or 1000 µg plasmid DNA (without the inserts). The DNA was injected intramuscularly (IM) in the quadriceps. Baboons were boosted with 500 or 1000 µg control plasmid DNA at weeks 4, 8, and 12. 500 µg is used in vaccinations across the board because in many nonhuman primate systems, this amount has provided consistent results.

Group 2: To determine the protective effect of Sm-p80 alone, the initial immunization was done with 500 µg plasmid Sm-p80-pcDNA3.1 or Sm-p80-VR1020. The DNA was injected IM in the quadriceps. Baboons were boosted with 500 µg Sm-p80-pcDNA3.1 or or Sm-p80-VR1020 at weeks 4, 8, and 12.

Group 3: To determine if by using IL-2 as genetic adjuvants, the protective effect of Sm-p80 can be enhanced, the initial immunization was carried out with 500 µg plasmid Sm-p80-pcDNA3 or Sm-p80-VR1020 and 500 µg plasmid pORF-hIL-2. The DNA was injected IM in the quadriceps. Baboons were boosted with 500 µg Sm-p80-pcDNA3.1 or Sm-p80-VR1020 and 500 µg pORF-hIL-2 at weeks 4, 8, and 12.

After 4 weeks of the final boost, baboons from all of the groups were challenged with a total of 1000 cercariae of *S. mansoni* by the abdominal pouch method. Eight weeks after the final challenge, the baboons were be immobilized and lightly anesthetized with a mixture of ketamine (Ketaminol—10 mg/kg body wt) and xylazine (0.5 mg/kg) and then deeply anesthetized by intravenous injection of heparinized sodium pentabarbitol solution. The animals were then euthanized by exsanguination from the heart ventricle. This method of euthanization favors quantitative adult worm recovery by perfusion and post-perfusion inspection of mesenteric veins. The adult parasites were recovered by perfusion from the mesenteric vasculature and hepatic portal system by modifications of published methods. Protection (P) will be calculated by comparing worm burdens from vaccinated (V) and control (C) baboons by a standard formula: % P=(C−V)/(C×100).

Protocols using prime boost and protein vaccination strategies in baboons were as follows:

The prime/boost approach which provides the optimal protection results in mice has been used in baboons. Animals first immunized with 500 µg plasmid DNA (Sm-p80-VR1020 or Immunostimulatory sequences (ISS)-Sm-p80-ISS-VR1020) and were boosted with 200 µg baculovirus generated recombinant Sm-p80 protein in the presence of either ODN #2138 (250 µg) or resiquimod (50 µg). Animals in the age-matched control group received similar amounts of plasmid DNA without inserts as animals in the experimental group and boosted with irrelevant BEVS-generated recombinant protein in the same adjuvant as in the experimental group. Antigen DNA alone (without the boost) and recombinant protein alone (without the prime) were also included as controls. Note that the ISS sequences used for generating the Sm-p80-ISS construct as well as CpG ODNs utilized in this study have consistently been shown to efficiently work in both mice and nonhuman-primates.

Reference is now made to FIG. 5-FIG. 24, which, in conjunction with Table 6-Table 24, detail experimental results derived from in vitro testing and in vivo testing in both mice and baboons. These experimental results demonstrate the efficacy of the present invention.

Figure 5:
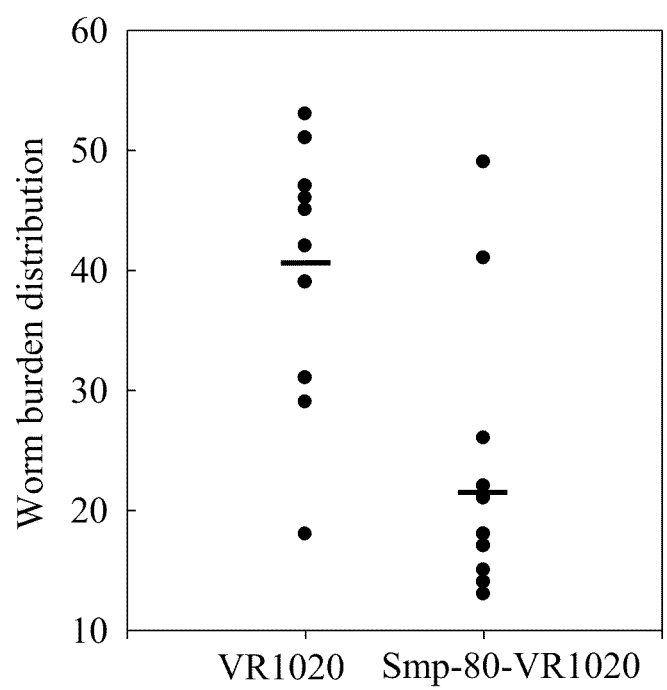
FIG. 5 is a depiction of the worm burden distribution for groups of mice immunized with control plasmids, VR1020 (n=10) and with Sm-p80-VR1020 (n=10). Reduction in worm burden was statistically lower in vaccinated animals (P<0.001)

Reference is now made to FIG. 5 in conjunction with Table 6, demonstrating the reduction in worm burden distribution for groups of mice immunized with control plasmids, VR1020 (n=10) and with Sm-p80-VR1020 (n=10). Mice immunized with Sm-p80-VR1020 showed 46.87% reduction in worm burden when compared to mice which received only control plasmids, VR1020. Reduction in worm burden was statistically significant in vaccinated animals (P<0.001).

TABLE 6

Anti-worm effect in C57BL/6 mice following immunization with Sm-p80-VR1020

| Immunization Groups | n | Worms burden (Mean ± S.E.) | % Reduction in worm burden (P < 0.001) |
|---|---|---|---|
| VR1020 | 15 | 40.53 ± 2.53 | — |
| Sm-p80-VR1020 | 15 | 21.53 ± 2.65 | 46.87% |

Figure 6:
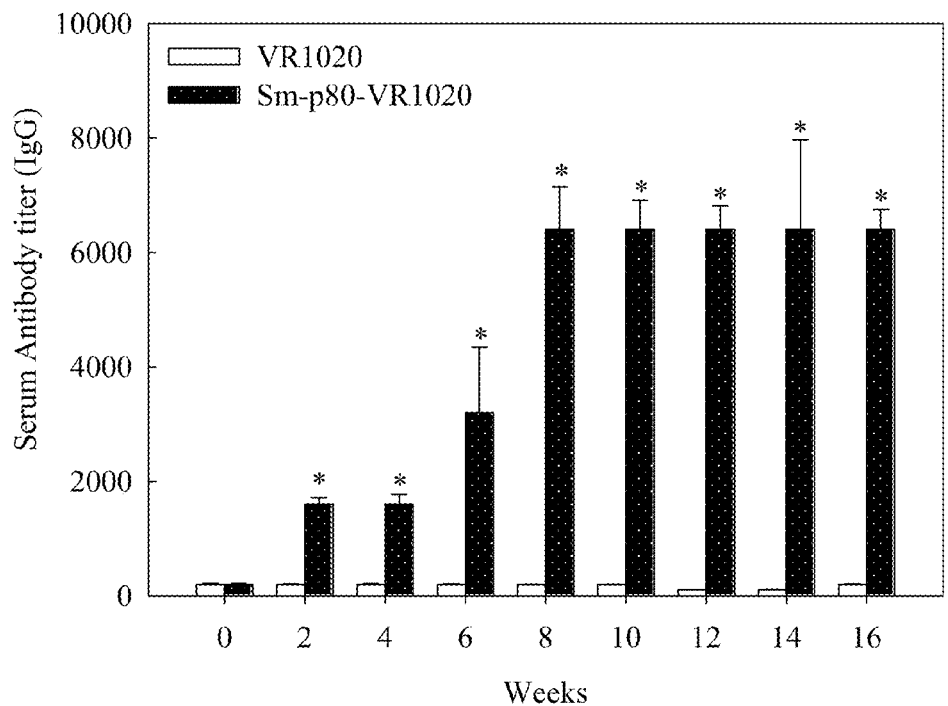
FIG. 6 is a depiction of the antibody titers of anti-Sm-p80 total IgG in immunized mice. ELISA was performed with a pool of sera obtained by mixing equal volumes of serum collected from each mouse (biweekly) in their respective groups (VR1020 and Sm-p80-VR1020). The values represent the mean of three experiments±standard deviation. Statistical significance (P≤0.05) are indicated by (*) compared with VR1020 group.

Reference is now made to FIG. 6, a graph of the antibody titers of anti-Sm-p80 total IgG in immunized mice. Table 7 lists serum antibody total IgG production induced by inoculation of recombinant Sm-p80 vaccine.

TABLE 7

Serum Antibody Total IgG production induced by inoculation of recombinant Sm-p80 vaccine

| Weeks | VR1020 | Sm-p80-VR1020 |
|---|---|---|
| 0 week | 200 ± 18.18 | 200 ± 18.2 |
| 2 week | 200 ± 9.85 | 1600 ± 119.63 |
| 4 week | 200 ± 15.23 | 1600 ± 174.26 |
| 6 week | 200 ± 10.00 | 3200 ± 1142.86 |

TABLE 7-continued

Serum Antibody Total IgG production induced
by inoculation of recombinant Sm-p80 vaccine

| Weeks | VR1020 | Sm-p80-VR1020 |
|---|---|---|
| 8 week | 200 ± 3.16 | 6400 ± 750.62 |
| 10 week | 200 ± 3.00 | 6400 ± 513.99 |
| 12 week | 100 ± 10.89 | 6400 ± 414.57 |
| 14 week | 100 ± 13.37 | 6400 ± 1565.01 |
| 16 week | 200 ± 11.06 | 6400 ± 356.32 |

Figure 7:
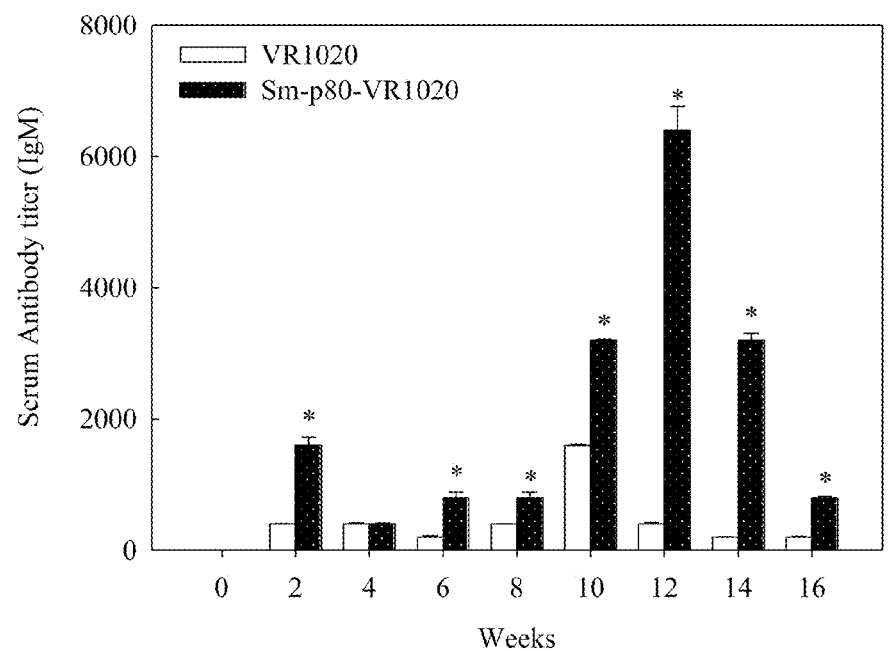
FIG. 7 is a depiction of the antibody titers of anti-Sm-p80 total IgM in immunized mice. ELISA was performed with a pool of sera obtained by mixing equal volumes of serum collected from each mouse (biweekly) in their respective groups (VR1020 and Sm-p80-VR1020). The values represent the mean of three experiments±standard deviation. Statistical significance (P≤0.05) are indicated by (*) compared with VR1020 group.

Reference is now made to FIG. 7, a graph of the antibody titers of anti-Sm-p80 total IgM in immunized mice. Table 8 lists serum antibody IgM production induced by inoculation of recombinant Sm-p80 vaccine.

TABLE 8

Serum Antibody IgG2a production induced by
inoculation of recombinant Sm-p80 vaccine

| Weeks | VR1020 | Sm-p80-VR1020 |
|---|---|---|
| 0 week | 100 ± 7.38 | 50 ± 5.00 |
| 2 week | 100 ± 8.33 | 50 ± 5.62 |
| 4 week | 100 ± 20.41 | 200 ± 48.08 |
| 6 week | 100 ± 5.24 | 800 ± 243.65 |
| 8 week | 100 ± 10.43 | 1600 ± 98.25 |
| 10 week | 100 ± 4.70 | 3200 ± 241.78 |
| 12 week | 100 ± 5.59 | 3200 ± 444.08 |
| 14 week | 100 ± 2.84 | 3200 ± 130.61 |
| 16 week | 100 ± 8.02 | 3200 ± 624.76 |

Figure 8:
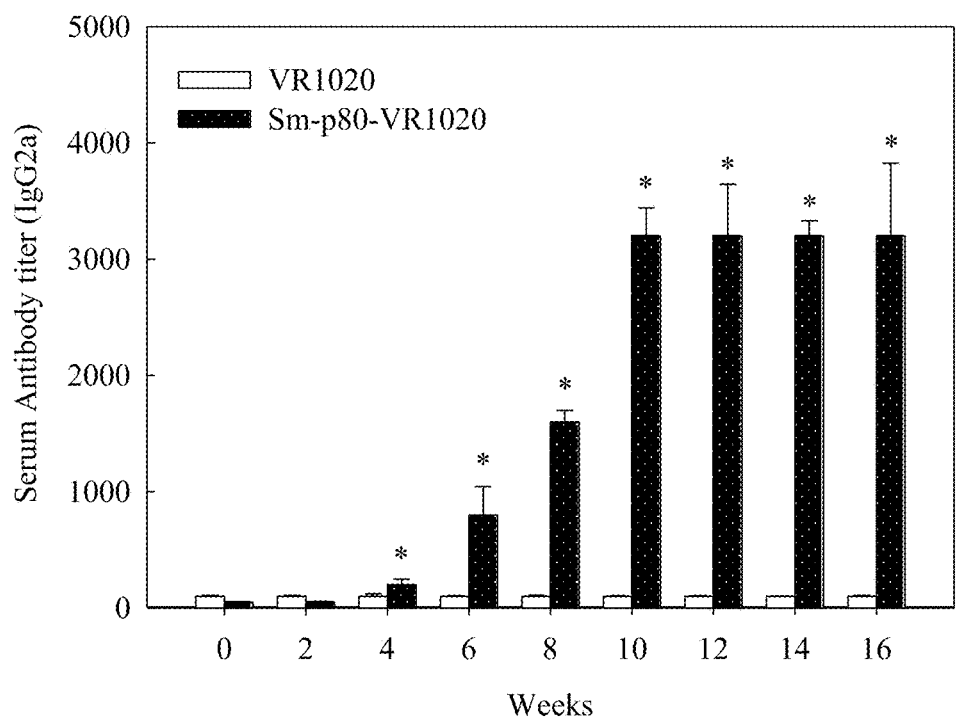
FIG. 8 is a depiction of the antibody titers of anti-Sm-p80 IgG2a in immunized mice. ELISA was performed with a pool of sera obtained by mixing equal volumes of serum collected from each mouse (biweekly) in their respective groups (VR1020 and Sm-p80-VR1020). The values represent the mean of three experiments±standard deviation. Statistical significance (P≤0.05) are indicated by (*) compared with VR1020 group.

Reference is now made to FIG. 8, a graph of the antibody titers of anti-Sm-p80 IgG2a in immunized mice. Table 9 lists serum antibody IgG2a production induced by inoculation of recombinant Sm-p80 vaccine.

TABLE 9

Serum Antibody IgM production induced by
inoculation of recombinant Sm-p80 vaccine

| Weeks | VR1020 | Sm-p80-VR1020 |
|---|---|---|
| 0 week | 0 ± 0 | 0 ± 0 |
| 2 week | 400 ± 5.59 | 1600 ± 118.86 |
| 4 week | 400 ± 20.51 | 400 ± 15.79 |
| 6 week | 200 ± 22.93 | 800 ± 85.46 |
| 8 week | 400 ± 1.18 | 800 ± 85.46 |
| 10 week | 1600 ± 16.45 | 3200 ± 14.75 |
| 12 week | 400 ± 26.44 | 6400 ± 362.81 |
| 14 week | 200 ± 7.67 | 3200 ± 101.73 |
| 16 week | 200 ± 14.17 | 800 ± 21.92 |

Figure 9:
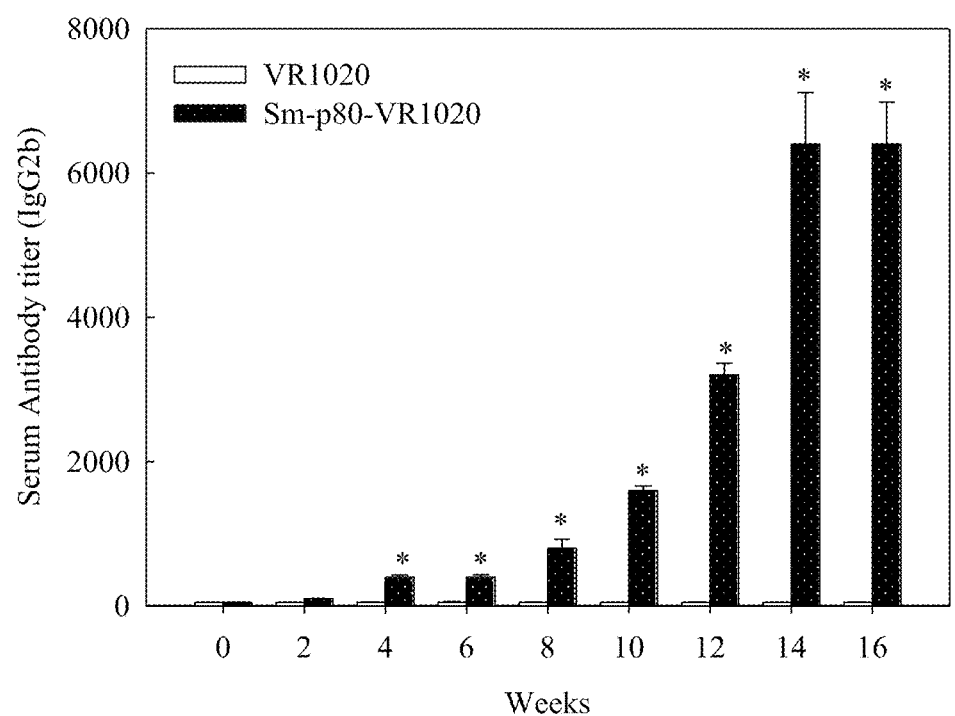
FIG. 9 is a depiction of the antibody titers of anti-Sm-p80 IgG2b in immunized mice. ELISA was performed with a pool of sera obtained by mixing equal volumes of serum collected from each mouse (biweekly) in their respective groups (VR1020 and Sm-p80-VR1020). The values represent the mean of three experiments±standard deviation. Statistical significance (P≤0.05) are indicated by (*) compared with VR1020 group.

Reference is now made to FIG. 9, a graph of the antibody titers of anti-Sm-p80 IgG2b in immunized mice. Table 10 lists serum antibody IgG2b production induced by inoculation of recombinant Sm-p80 vaccine.

TABLE 10

Serum Antibody IgG2b production induced by
inoculation of recombinant Sm-p80 vaccine

| Weeks | VR1020 | Sm-p80-VR1020 |
|---|---|---|
| 0 week | 50 ± 1.31 | 50 ± 2.76 |
| 2 week | 50 ± 0.90 | 100 ± 5.68 |
| 4 week | 50 ± 4.65 | 400 ± 30.94 |
| 6 week | 50 ± 11.72 | 400 ± 33.52 |
| 8 week | 50 ± 5.72 | 800 ± 124.06 |
| 10 week | 50 ± 0.95 | 1600 ± 63.05 |
| 12 week | 50 ± 6.37 | 3200 ± 162.96 |
| 14 week | 50 ± 1.39 | 6400 ± 716.8 |
| 16 week | 50 ± 5.06 | 6400 ± 581.82 |

Figure 10:
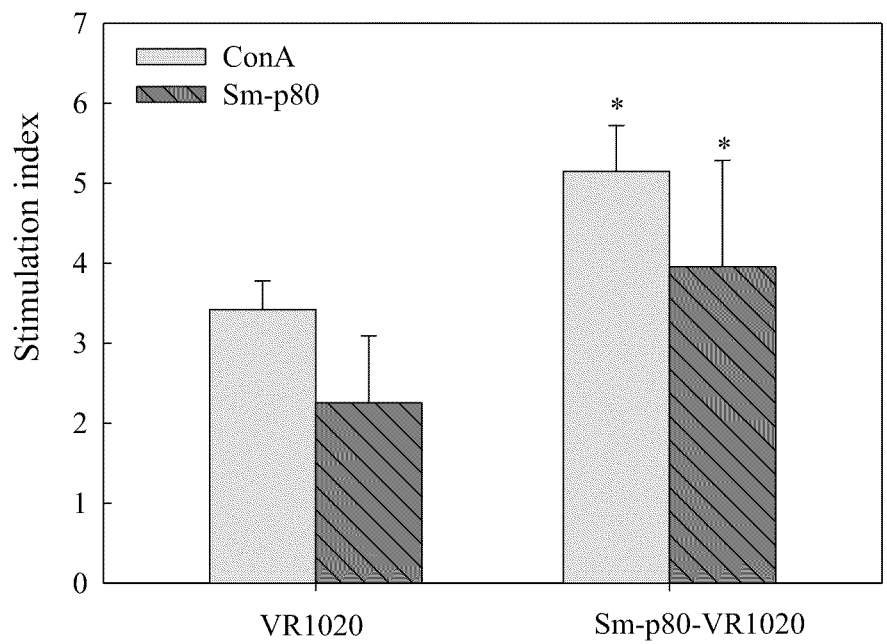
FIG. 10 is a depiction of splenocyte proliferation induced by recombinant Sm-p80 compared to the stimulation induced by Concanavalin A after 48 hours of culturing in vitro.
Figure 11:
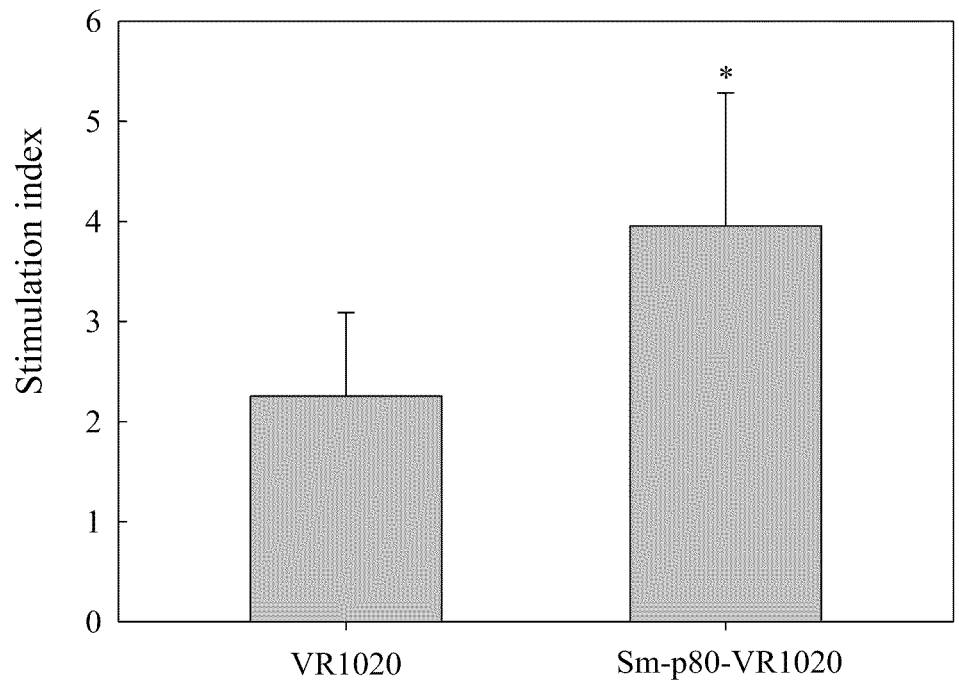
FIG. 11 is a depiction of splenocyte proliferation induced by recombinant Sm-p80 after 48 hours of culturing in vitro.

Reference is now made to FIG. 10 and FIG. 11, in conjunction with Table 11, demonstrating splenocyte proliferation induced by recombinant Sm-p80 compared to stimulation induced by Concanavalin A after 48 hours of culturing in vitro.

TABLE 11

Splenocyte proliferation induced by recombinant
Sm-p80 after 48 hrs of culturing in vitro.

Figure 12:
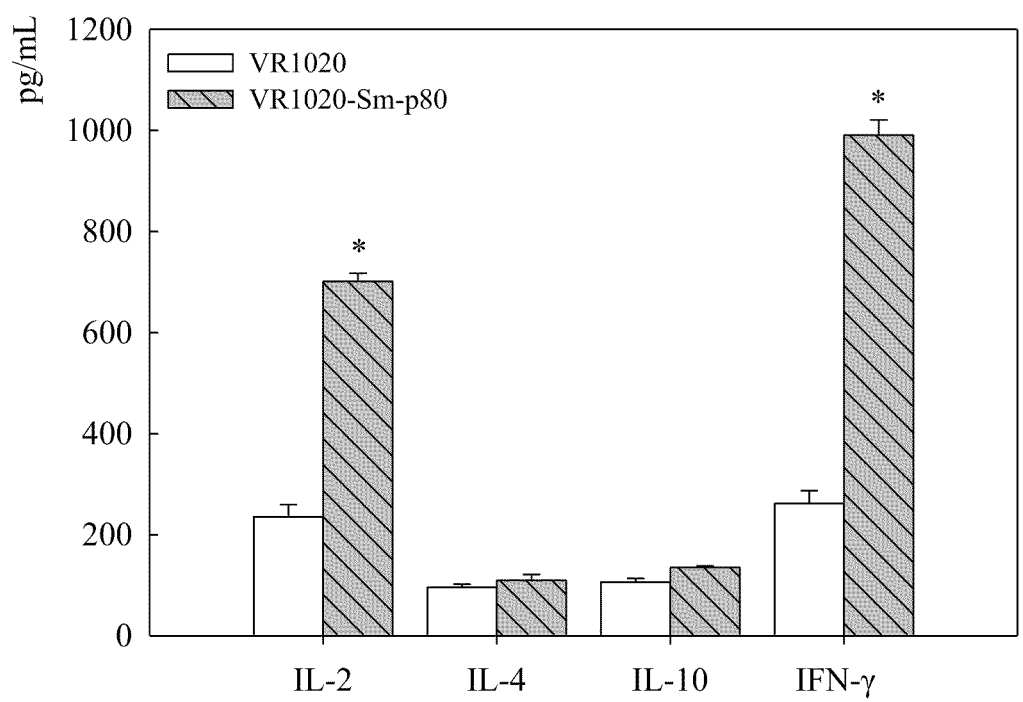
FIG. 12 is a depiction of levels of cytokine production by splenocytes after 48 hours of stimulation with recombinant Sm-p80 in vitro. Groups of mice were inoculated with VR1020 and VR1020-Sm-p80. Data are shown as mean±standard deviation. Statistical significance (P≤0.05) are indicated by (*) compared with VR1020 group using independent sample test.
Figure 13A:
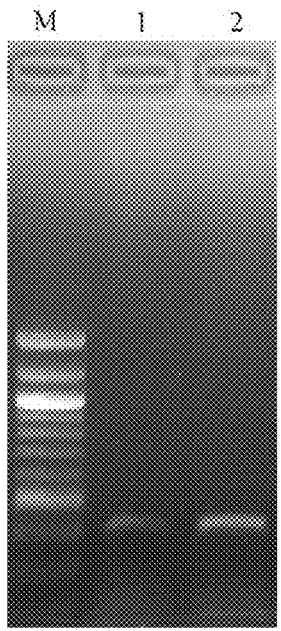
FIG. 13A is a depiction of an agarose gel following RT-PCR (Interleukin 6). M=100 bp marker; 1=IL-6 (VR1020 group); 2=IL-6 (VR1020-Sm-p80 group)
Figure 13B:
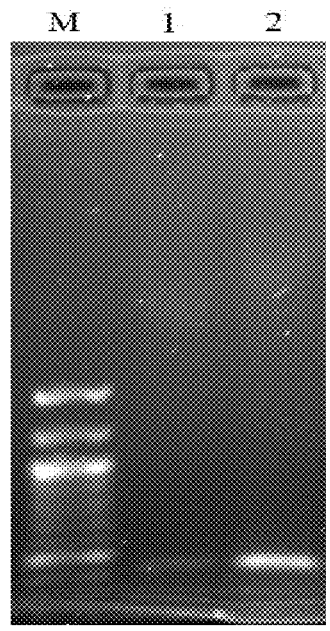
FIG. 13B is a depiction of an agarose gel following RT-PCR (Interleukin 6). M=100 bp marker; 1=IL-6 (VR1020 group); 2=IL-6 (VR1020-Sm-p80 group)
Figure 13C:
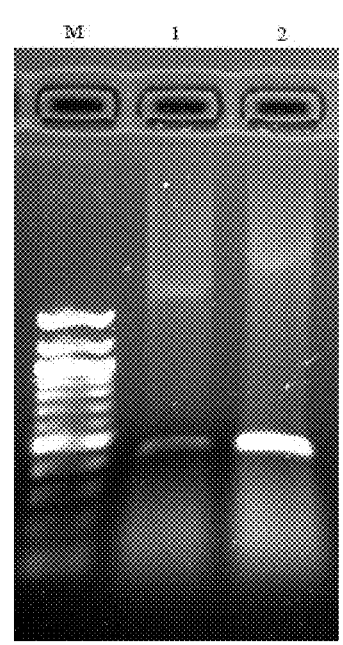
FIG. 13C is a depiction of an agarose gel following RT-PCR (Interleukin 6). M=100 bp marker; 1=IL-6 (VR1020 group); 2=IL-6 (VR1020-Sm-p80 group)
Figure 14A:
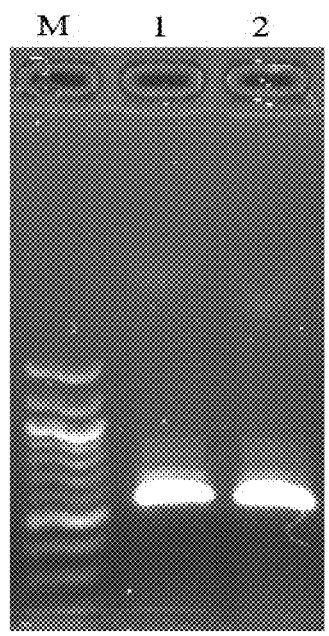
FIG. 14A is a depiction of an agarose gel following RT-PCR (glyceraldehyde 3-phosphate dehydrogenase). M=100 bp marker; 1=GAPDH (VR1020 group); 2=GAPDH (VR1020-Sm-p80 group)
Figure 14B:
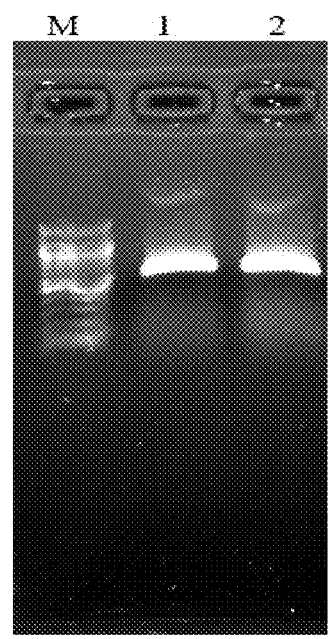
FIG. 14B is a depiction of an agarose gel following RT-PCR (glyceraldehyde 3-phosphate dehydrogenase). M=100 bp marker; 1=GAPDH (VR1020 group); 2=GAPDH (VR1020-Sm-p80 group)
Figure 15:
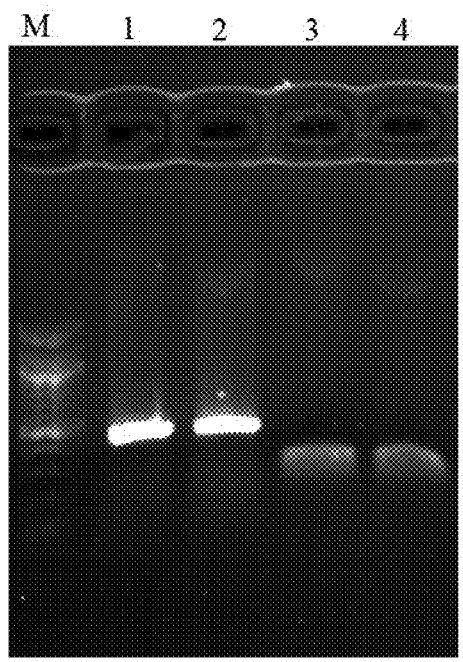
FIG. 15 is a depiction of an agarose gel following RT-PCR (glyceraldehyde 3-phosphate dehydrogenase and Interleukin 1 alpha). M=100 bp marker; 1=GAPDH (VR1020 group); 2=GAPDH (VR1020-Sm-p80 group); 3=IL-1α (VR1020 group); 4=IL-1α (VR1020-Sm-p80 group)
Figure 16:
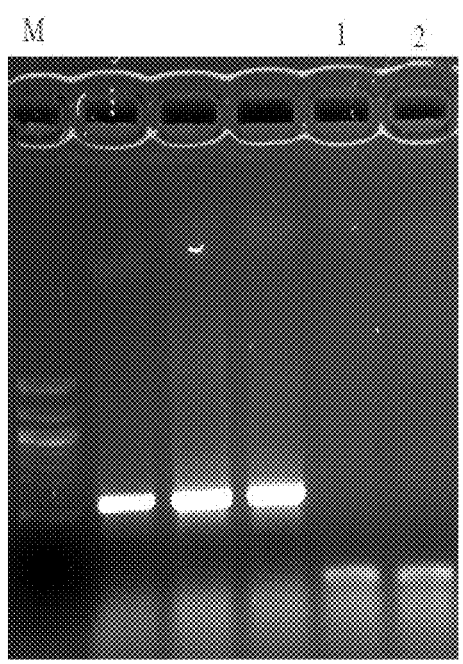
FIG. 16 is a depiction of a an agarose gel following RT-PCR (Interleukin 1 alpha). M=100 bp marker; 1=IL-1α (VR1020 group); 2=IL-1α (VR1020-Sm-p80 group)
Figure 17:
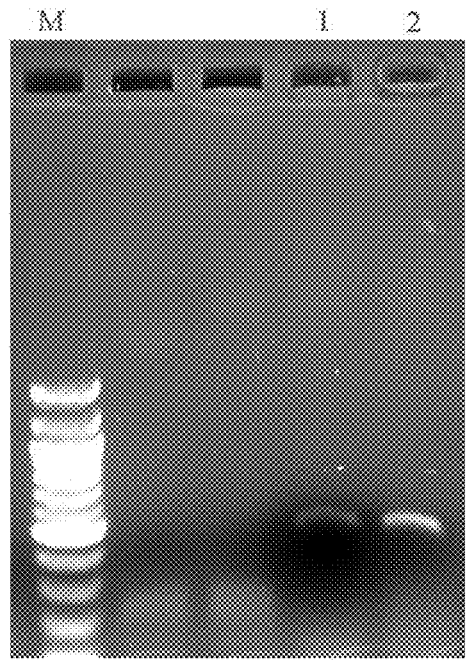
FIG. 17 is a depiction of an agarose gel following RT-PCR (Interferon gamma). M=100 bp marker; 1=IFN-γ (VR1020 group); 2=IFN-γ (VR1020-Sm-p80 group)
Figure 18:
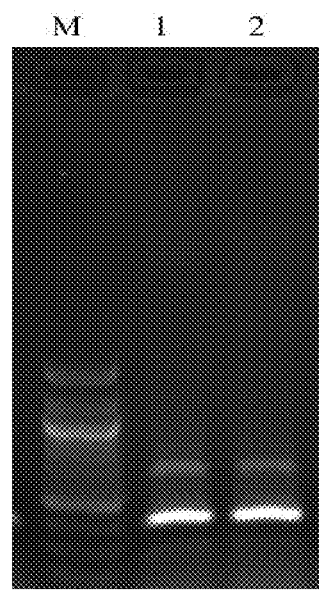
FIG. 18 is a depiction of an agarose gel following RT-PCR (Interleukin 4). M=100 bp marker; 1=IL-4 (VR1020 group); 2=IL-4 (VR1020-Sm-p80 group)
Figure 19:
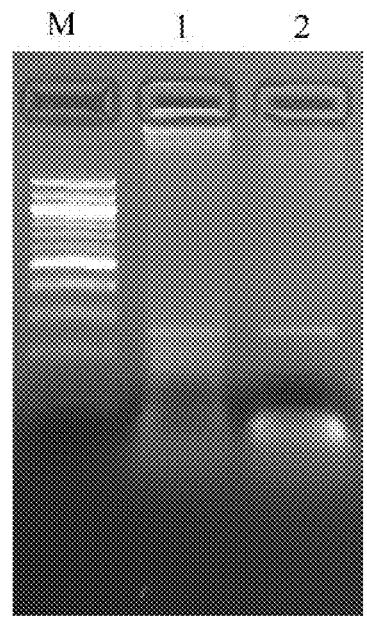
FIG. 19 is a depiction of an agarose gel following RT-PCR (Interleukin 5). M=100 bp marker; 1=IL-5 (VR1020 group); 2=IL-5 (VR1020-Sm-p80 group)
Figure 20:
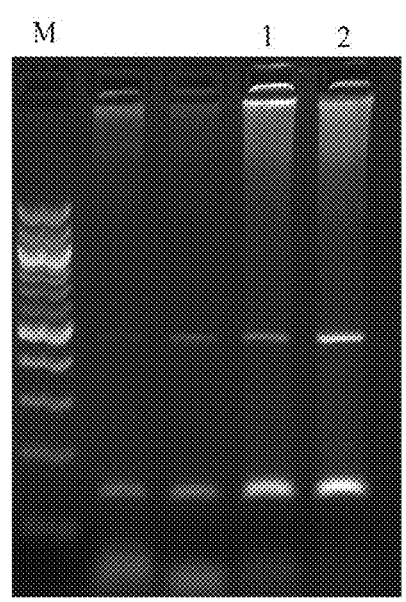
FIG. 20 is a depiction of an agarose gel following RT-PCR (Interleukin 17). M=100 bp marker; 1=IL-17 (VR1020 group); 2=IL-17 (VR1020-Sm-p80 group)
Figure 21:
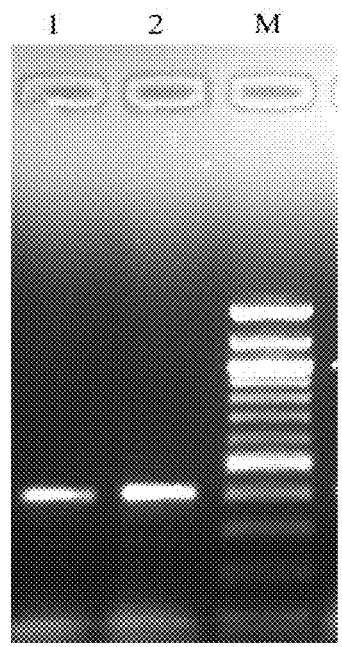
FIG. 21 is a depiction of an agarose gel following RT-PCR (Interleukin 2). M=100 bp marker; 2=IL-2 (VR1020-Sm-p80 group); 1=IL-2 (VR1020 group)
Figure 22:
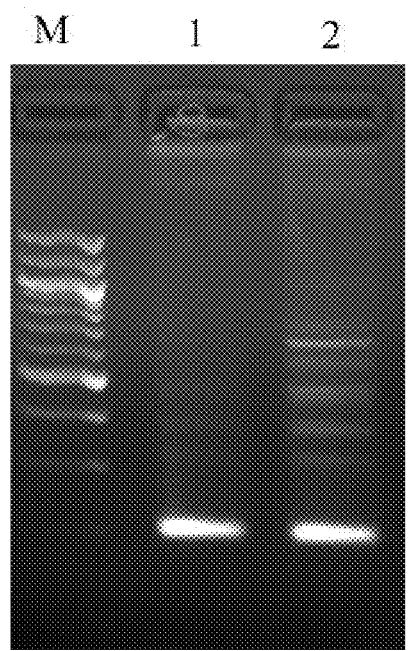
FIG. 22 is a depiction of an agarose gel following RT-PCR (Tumor necrosis factor alpha). M=100 bp marker; 1=TNF-α (VR1020 group); 2=TNF-α (VR1020-Sm-p80 group)
Figure 23:
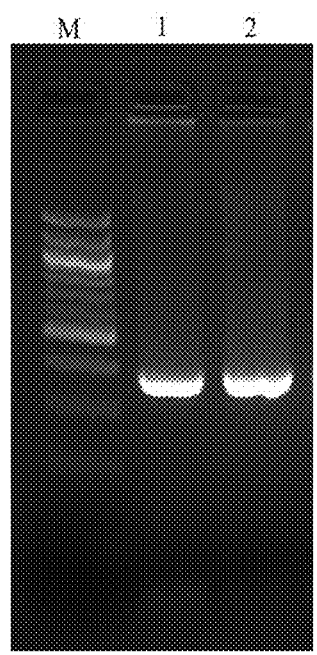
FIG. 23 is a depiction of an agarose gel following RT-PCR (Interleukin 1 beta). M=100 bp marker; 1=IL-1β (VR1020 group); 2=IL-1β (VR1020-Sm-p80 group)
Figure 24:
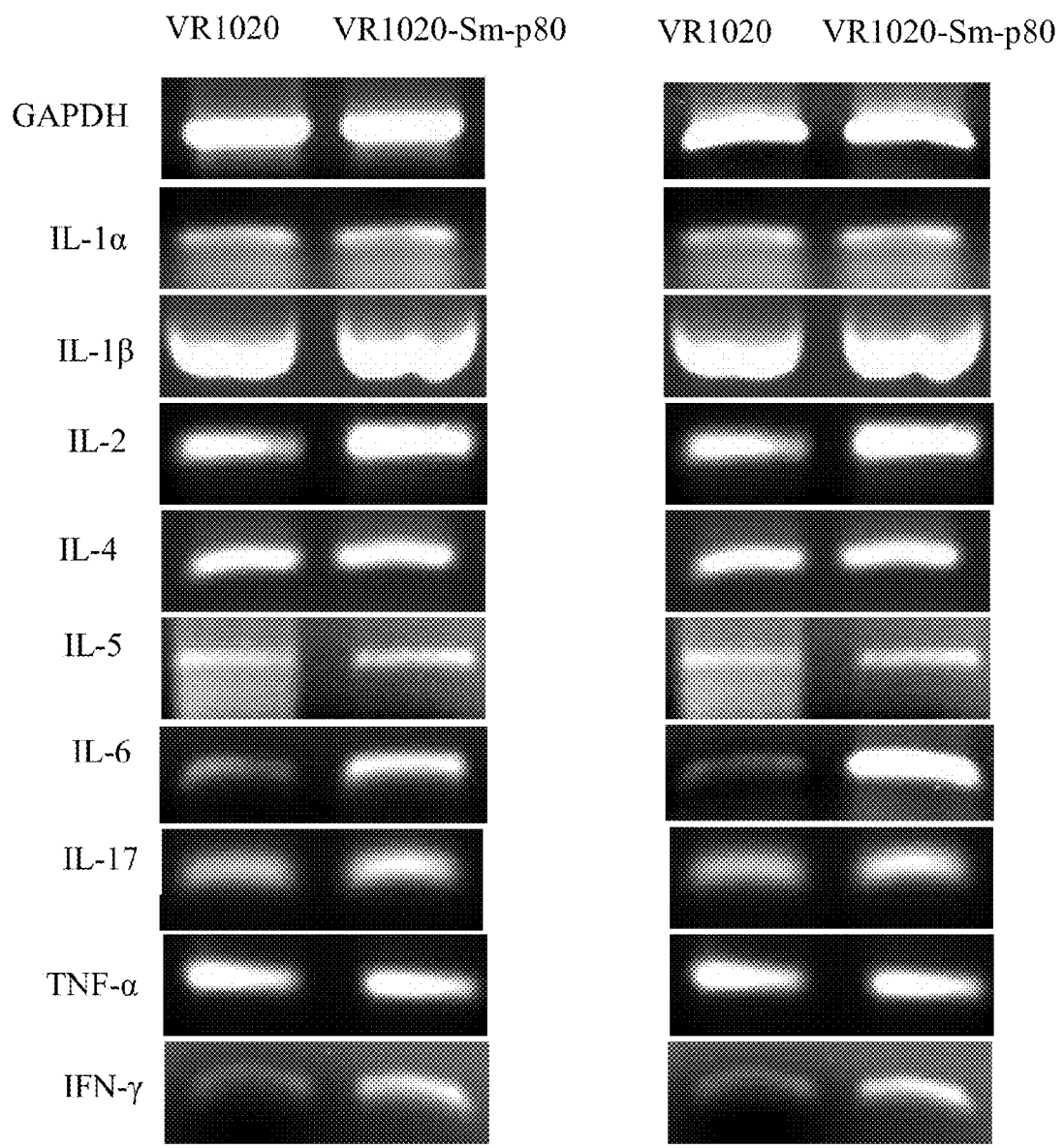
FIG. 24 is a depiction of an agarose gel following RT-PCR (GAPDH, IL-1α, IL-1β, IL-2, IL-4, IL-5, IL-6, IL-17, and TNF-α) in the VR1020 group and VR1020-Sm-p80 group.
Figure 25:
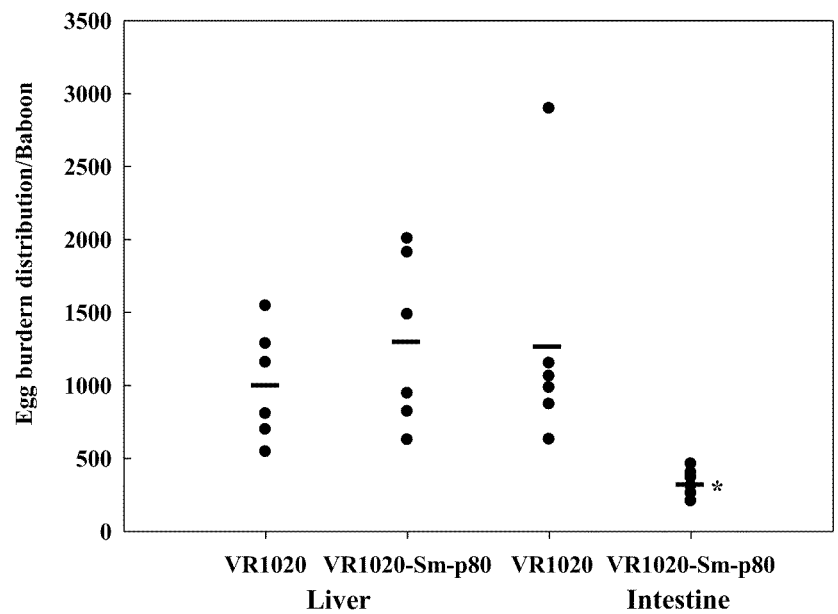
FIG. 25 is a depiction of egg load per gram of liver and intestine of individual baboons for groups of baboons immunized with control plasmids, VR1020 (n=6) and with VR1020-Sm-p80 (n=6). Reductions in egg counts were statistically lower in vaccinated animals (P<0.05)
Figure 26:
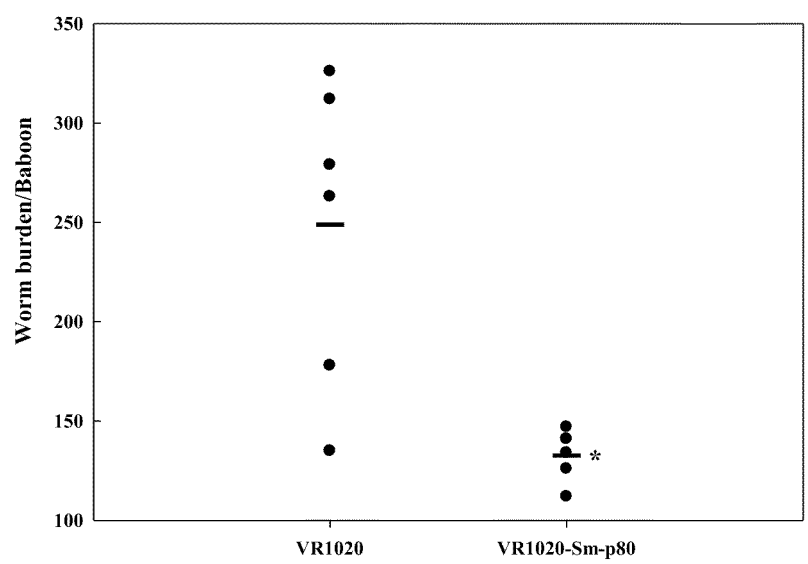
FIG. 26 is a depiction of worm burden distribution for groups of baboons immunized with control plasmids, VR1020 (n=6) and with VR1020-Sm-p80 (n=6). Reductions in worm burden were statistically lower in vaccinated animals (P<0.05).

| Groups | Stimulation index(SI) | |
|---|---|---|
| | ConA | Sm-p80 |
| VR1020 | 3.42 ± 0.36 | 2.26 ± 0.83 |
| Sm-p80-VR1020 | 5.15 ± 0.57* | 3.96 ± 1.33* | a The values in the table represent mean ± S.D.
*$P \leq 0.047$ vs. pcDNA3 group stimulated by recombinant Sm-p80 respectively using independent samples test Reference is now made to FIG. 12, depicting levels of cytokine production by splenocytes after 48 hours of stimulation with recombinant Sm-p80 in vitro (See also Table 12). Groups of mice were inoculated with VR1020 and VR1020-Sm-p80. Data are shown as mean±standard deviation. Statistical significance ($P \leq 0.05$) are indicated by (*) compared with VR1020 group using independent sample test.

TABLE 12

Levels of cytokine production by splenocytes after 48
hr stimulation with recombinant Sm-p80 in vitro.[a]

| Group | IL-2(pg/mL) | IL-4(pg/mL) | IL-10(pg/mL) | IFN-γ(pg/mL) |
|---|---|---|---|---|
| VR1020 | 234.88 ± 24.66 | 95.62 ± 6.19 | 105.78 ± 7.50 | 261.45 ± 25.69 |
| VR1020-Sm-p80 | 701.43 ± 15.76* | 109.07 ± 11.99 | 135.30 ± 2.58 | 990.78 ± 30.10* |

[a]The values in the table represent mean ± S.D.
*$P \leq 0.05$ vs. VR1020 group stimulated by recombinant Sm-p80 respectively using independent sample test Reference is now made to FIG. 13-FIG. 24, depicting agarose gel electrophoresis of various cytokines (GAPDH, IL-1α, IL-1β, IL-2, IL-4, IL-5, IL-6, IL-17, and TNF-α) estimated in the VR1020 group and VR1020-Sm-p80 group of immunized mice. Table 13 quantitatively analyzes the various cytokines estimated in VR1020 and VR1020-Sm-p80 immunized mice.

TABLE 13

Quantitative analysis of various cytokines estimated in VR1020 and VR1020-Sm-p80 immunized mice.

| Cytokine | VR1020 | VR1020-Sm-p80 |
|---|---|---|
| GAPDH(μg/mL) | 7.89 ± 1.72 | 8.54 ± 2.29 |
| IL-1α(μg/mL) | 4.73 ± 2.02 | 5.46 ± 1.84 |
| IL-1β(μg/mL) | 11.98 ± 0.17 | 12.46 ± 1.22 |

TABLE 13-continued

Quantitative analysis of various cytokines estimated in VR1020 and VR1020-Sm-p80 immunized mice.

| Cytokine | VR1020 | VR1020-Sm-p80 |
|---|---|---|
| IL-2(μg/mL) | 3.68 ± 0.94 | 4.82 ± 0.14 |
| IL-4(μg/mL) | 13.54 ± 4.25 | 13.01 ± 0.38 |
| IL-5(μg/mL) | 2.28 ± 1.23 | 2.59 ± 0.58 |
| IL-6(μg/mL) | 2.47 ± 0.97 | 7.58 ± 4.37 |
| IL-17(μg/mL) | 4.55 ± 1.67 | 6.28 ± 1.97 |
| IFN-γ(μg/mL) | 1.01 ± 0.01 | 3.08 ± 0.13 |
| TNF-α(μg/mL) | 8.89 ± 3.44 | 9.08 ± 3.59 |

Table 14 summarizes production of serum antibody titers in baboons in the control group vaccinated with VR1020 and production of serum antibody titers in baboons in the experimental group vaccinated with VR1020-Sm-p80.

TABLE 14

Summary of the serum antibody titers in control (VR1020 vaccinated) and experimental (VR1020-Sm-p80 vaccinated) baboons

| Weeks | VR1020 | | | | | VR1020-Sm-p80 | | | | |
|---|---|---|---|---|---|---|---|---|---|---|
| | IgG | IgG1 | IgG2 | IgA | IgM | Total IgG | IgG1 | IgG2 | IgA | IgM |
| 0 week | 50 ± 4.07 | 50 ± 4.07 | 50 ± 3.31 | 300 ± 5.29 | 0.00 ± 0.00 | 400 ± 23.36 | 400 ± 23.36 | 50 ± 1.28 | 566.67 ± 14.82 | 0.00 ± 0.00 |
| 2 week | 50 ± 1.26 | 50 ± 4.37 | 50 ± 5.95 | 366.67 ± 21.82 | 0.00 ± 0.00 | 1000 ± 21.36 | 2266.67 ± 88.56 | 50 ± 2.72 | 866.67 ± 22.33 | 683.33 ± 149.17 |
| 4 week | 50 ± 1.76 | 50 ± 5.57 | 50 ± 1.56 | 250 ± 23.03 | 0.00 ± 0.00 | 21333.33 ± 320.00 | 3733.33 ± 118.54 | 1466.67 ± 58.65 | 1800 ± 77.68 | 1133.33 ± 233.37 |
| 6 week | 50 ± 2.24 | 50 ± 2.98 | 50 ± 1.02 | 266.67 ± 10.56 | 0.00 ± 0.00 | 34133.33 ± 981.33 | 6400 ± 415.21 | 3466.67 ± 233.91 | 4666.67 ± 88.67 | 3200 ± 681.48 |
| 8 week | 50 ± 3.44 | 50 ± 0.73 | 50 ± 1.60 | 366.67 ± 21.52 | 0.00 ± 0.00 | 20533.33 ± 496.00 | 3333.33 ± 182.63 | 2933.33 ± 243.63 | 5333.33 ± 297.85 | 933.33 ± 232.05 |

Table 15 and Table 16 summarize levels of cytokines produced by splenocytes after 48 hours of stimulation with recombinant Sm-p80 in vitro. Groups of baboons were inoculated with VR1020 (control group) and VR1020-Sm-p80 (experimental group). Data are shown as mean±standard deviation.

TABLE 15

Cytokine production of splenocytes induced by recombinant Sm-p80 after 48 hrs of culturing in vitro

| Vaccine group | IL-4(pg/mL) | IL-10(pg/mL) | IL-2(pg/mL) | IFN-γ(pg/mL) |
|---|---|---|---|---|
| VR1020 | 52.42 ± 2.42 | 53.99 ± 5.35 | 55.33 ± 14.30 | 72.89 ± 42.93 |
| Sm-p80-VR1020 | 54.18 ± 7.14 | 49.03 ± 9.64 | 447.01 ± 226.96 | 692.09 ± 321.73 | a The values in the table represent mean ± S.D.

TABLE 16

Cytokine production of splenocytes induced by recombinant Sm-p80 after 48 hrs of culturing in vitro

| Baboon name | Age in years | sex | Vaccine group | IL-4(pg/mL) | IL-10(pg/mL) | IL-2(pg/mL) | IFN-γ(pg/mL) |
|---|---|---|---|---|---|---|---|
| Jessie | 13.6 | female | VR1020 | 50.50 ± 0.63 | 49.17 ± 0.53 | 79.17 ± 59.48 | 83.82 ± 3.24 |
| Wendy | 12.4 | female | VR1020 | 52.66 ± 0.91 | 54.27 ± 1.51 | 49.62 ± 1.92 | 55.47 ± 2.89 |
| Trudy | 5.5 | female | VR1020 | 50.20 ± 0.95 | 48.42 ± 1.89 | 42.38 ± 0.86 | 30.55 ± 0.88 |

TABLE 16-continued

Cytokine production of splenocytes induced by recombinant Sm-p80 after 48 hrs of culturing in vitro

| Baboon name | Age in years | sex | Vaccine group | IL-4(pg/mL) | IL-10(pg/mL) | IL-2(pg/mL) | IFN-γ(pg/mL) |
|---|---|---|---|---|---|---|---|
| Josie | 6.5 | female | VR1020 | 52.35 ± 1.22 | 51.50 ± 1.04 | 47.54 ± 1.00 | 61.77 ± 5.08 |
| Magna | 13.6 | female | VR1020 | 56.93 ± 1.99 | 61.58 ± 1.68 | 66.38 ± 1.68 | 153.26 ± 3.84 |
| Maggie | 9.3 | female | VR1020 | 51.88 ± 0.92 | 58.98 ± 2.19 | 46.91 ± 0.76 | 52.48 ± 3.18 |
| Mocha | 5.3 | female | Sm-p80-VR1020 | 49.60 ± 4.19 | 42.40 ± 1.25 | 322.51 ± 7.46 | 790.61 ± 20.62 |
| Roxanne | 6.4 | female | Sm-p80-VR1020 | 50.35 ± 3.17 | 44.41 ± 2.87 | 433.78 ± 14.05 | 729.99 ± 16.09 |
| Louise | 9.9 | female | Sm-p80-VR1020 | 68.55 ± 8.90 | 68.40 ± 0.71 | 657.93 ± 17.92 | 871.24 ± 31.33 |
| Chaquita | 6.6 | female | Sm-p80-VR1020 | 52.82 ± 4.53 | 45.38 ± 16.5 | 659.69 ± 31.98 | 605.30 ± 38.60 |
| Babydoll | 10.7 | female | Sm-p80-VR1020 | 51.88 ± 4.30 | 47.53 ± 5.50 | 68.18 ± 4.81 | 108.34 ± 6.43 |
| Precious | 11.6 | female | Sm-p80-VR1020 | 51.88 ± 5.22 | 46.08 ± 1.70 | 539.96 ± 11.77 | 1047.0781 ± 75.48 | a The values in the table represent mean ± S.D.

Table 17 and Table 18 summarize levels of cytokines produced by peripheral blood mononuclear cells after 48 hours of stimulation with recombinant Sm-p80 in vitro. Groups of baboons were inoculated with VR1020 (control group) and VR1020-Sm-p80 (experimental group). Data are shown as mean±standard deviation.

Table 19 and Table 20 summarize Interleukin 4 and Interferon gamma spot-forming units (SFUs) induced by recombinant Sm-p80 after 48 hours of culturing in vitro. Each baboon was inoculated with VR1020 (control group) or VR1020-Sm-p80 (experimental group). Data are shown as mean±standard deviation.

TABLE 17

Cytokine production of PBMCs induced by recombinant Sm-p80 after 48 hrs of culturing in vitro

| Vaccine group | IL-4(pg/mL) | IL-10(pg/mL) | IL-2(pg/mL) | IFN-γ(pg/mL) |
|---|---|---|---|---|
| VR1020 | 7.91 ± 0.21 | 0.82 ± 0.61 | 7.03 ± 0.22 | 28.02 ± 0.67 |
| Sm-p80-VR1020 | 9.65 ± 1.56 | 0.71 ± 0.23 | 579.77 ± 51.25 | 384.21 ± 36.64 | a The values in the table represent mean ± S.D.

TABLE 18

Cytokine production of PBMCs induced by recombinant Sm-p80 after 48 hrs of culturing in vitro

| Baboon name | Age in years | sex | Vaccine group | IL-4(pg/mL) | IL-10(pg/mL) | IL-2(pg/mL) | IFN-γ(pg/mL) |
|---|---|---|---|---|---|---|---|
| Jessie | 13.6 | female | VR1020 | 7.88 ± 0.17 | 1.95 ± 0.04 | 7.16 ± 0.05 | 27.94 ± 0.31 |
| Wendy | 12.4 | female | VR1020 | 8.27 ± 0.49 | 0.92 ± 0.01 | 7.08 ± 0.21 | 27.66 ± 0.31 |
| Trudy | 5.5 | female | VR1020 | 7.76 ± 0.30 | 0.42 ± 0.03 | 6.90 ± 0.27 | 27.85 ± 0.47 |
| Josie | 6.5 | female | VR1020 | 7.68 ± 0.07 | 0.91 ± 0.04 | 7.37 ± 0.05 | 29.37 ± 0.61 |
| Magna | 13.6 | female | VR1020 | 7.95 ± 0.17 | 0.38 ± 0.00 | 6.77 ± 0.16 | 27.57 ± 0.32 |
| Maggie | 9.3 | female | VR1020 | 7.90 ± 0.53 | 0.36 ± 0.10 | 6.87 ± 0.16 | 27.75 ± 0.63 |
| Mocha | 5.3 | female | Sm-p80-VR1020 | 8.12 ± 0.13 | 0.74 ± 0.10 | 608.74 ± 26.66 | 332.53 ± 10.45 |
| Roxanne | 6.4 | female | Sm-p80-VR1020 | 11.09 ± 0.10 | 0.97 ± 0.05 | 640.87 ± 11.77 | 331.02 ± 9.23 |
| Louise | 9.9 | female | Sm-p80-VR1020 | 11.09 ± 0.22 | 0.97 ± 0.11 | 613.23 ± 20.00 | 420.53 ± 18.54 |
| Chaquita | 6.6 | female | Sm-p80-VR1020 | 11.02 ± 0.10 | 0.59 ± 0.05 | 517.85 ± 25.44 | 367.32 ± 27.21 |
| Babydoll | 10.7 | female | Sm-p80-VR1020 | 8.61 ± 0.62 | 0.40 ± 0.03 | 519.75 ± 10.76 | 468.27 ± 15.59 |
| Precious | 11.6 | female | Sm-p80-VR1020 | 8.00 ± 0.66 | 0.58 ± 0.01 | 578.21 ± 14.75 | 385.60 ± 36.64 | a The values in the table represent mean ± S.D.

TABLE 19

IFN-γ and IL-4 SFU induced by recombinant Sm-p80 after 48 hrs of culturing in vitro

| Vaccine group | ConA | | Sm-p80 | | Chicken egg albumin | | No stimuli | |
|---|---|---|---|---|---|---|---|---|
| | IL-4 | IFN-γ | IL-4 | IFN-γ | IL-4 | IFN-γ | IL-4 | IFN-γ |
| VR1020 | 171.67 ± 45.90 | 247.92 ± 15.21 | 6.17 ± 1.31 | 29.5 ± 12.87 | 7.25 ± 2.82 | 17.75 ± 6.04 | 5.33 ± 0.77 | 20.42 ± 6.35 |
| Sm-p80-VR1020 | 154.75 ± 32.86 | 302.33 ± 18.43 | 6.17 ± 1.13 | 129.25 ± 38.71* | 6.58 ± 1.31 | 90.92 ± 32.81 | 6.17 ± 0.74 | 78.33 ± 31.57* | a The values in the table represent mean ± S.E.
*$P \leq 0.05$ vs. VR1020 group stimulated by recombinant Sm-p80 respectively using independent samples test

TABLE 20

IFN-γ and IL-4 SFU induced by recombinant Sm-p80 after 48 hrs of culturing in vitro

| Baboon name | Code number | sex | Vaccine group | IL-4 | IFN-γ |
|---|---|---|---|---|---|
| Jessie | 37-6 | female | VR1020 | 9.5 ± 2.12 | 31.0 ± 0.71 |
| Wendy | 62-90 | female | VR1020 | 7.5 ± 2.12 | 4.0 ± 7.00 |
| Trudy | 1603 | female | VR1020 | 6.0 ± 1.41 | 0.0 ± 0.00 |
| Josie | 1202 | female | VR1020 | 8.5 ± 9.19 | 43.0 ± 22.63 |
| Magna | PC9502 | female | VR1020 | 0.5 ± 0.71 | 0.0 ± 0.00 |
| Maggie | 1299 | female | VR1020 | 5.0 ± 0.00 | 0.0 ± 0.00 |
| Mocha | 3403 | female | Sm-p80-VR1020 | 11.0 ± 4.24 | 55.0 ± 50.21 |
| Roxanne | 3402 | female | Sm-p80-VR1020 | 7.5 ± 7.78 | 31.5 ± 8.49 |
| Louise | 2798 | female | Sm-p80-VR1020 | 6.0 ± 0.00 | 67.5 ± 6.36 |
| Chaquita | 402 | female | Sm-p80-VR1020 | 3.5 ± 0.71 | 67.0 ± 30.41 |
| Babydoll | 3397 | female | Sm-p80-VR1020 | 4.0 ± 2.83 | 0.0 ± 0.00 |
| Precious | 57-288 | female | Sm-p80-VR1020 | 5.0 ± 2.83 | 89.5 ± 24.04 | a The values in the table represent mean ± S.D.

The disclosed vaccine compositions and methods of use are generally described, with examples incorporated as particular embodiments of the invention and to demonstrate the practice and advantages thereof. It is understood that the examples are given by way of illustration and are not intended to limit the specification or the claims in any manner.

To facilitate the understanding of this invention, a number of terms may be defined below. Terms defined herein have meanings as commonly understood by a person of ordinary skill in the areas relevant to the present invention. Terms such as "a," "an," and "the" are not intended to refer to only a singular entity, but include the general class of which a specific example may be used for illustration. The terminology herein is used to describe specific embodiments of the invention, but their usage does not delimit the disclosed method, except as may be outlined in the claims.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures and vaccine compositions described herein. Such equivalents are considered to be within the scope of this invention and are covered by the claims.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of" respectively, shall be closed or semi-closed transitional phrases.

All of the vaccine compositions and/or methods of use disclosed and claimed herein can be made and executed without undue experimentation in light of the present disclosure. While the vaccine compositions and methods of use of this invention have been described in terms of preferred embodiments, it will be apparent to those skilled in the art that variations may be applied to the vaccine compositions and/or methods of use and in the steps or in the sequence of steps of the method described herein without departing from the concept, spirit, and scope of the invention.

More specifically, it will be apparent that certain components which are both related by material and function may be substituted for the components described herein while the same or similar results would be achieved. All such similar substitutes and modifications apparent to those skilled in the art are deemed to be within the spirit, scope, and concept of the invention as defined by the appended claims.

REFERENCES

1. Gryseels B, Polman K, Clerinx J, Kestens L. Human schistosomiasis. Lancet 2006; 368(September (9541)):1106-18.
2. Steinmann P, Keiser J, Bos R, Tanner M, Utzinger J. Schistosomiasis and water resources development: systematic review, meta-analysis, and estimates of people at risk. Lancet Infect Dis 2006; 6(July (7)):411-25.
3. Bergquist R, Al-Sherbiny M, Barakat R, Olds R. Blueprint for schistosomiasis vaccine development. Acta Trop 2002; 82(May (2)):183-92.
4. Siddiqui A A, Ahmad G, Damian R T, Kennedy R C. Experimental vaccines in animal models for schistosomiasis. Parasitol Res 2008; 102(April (5)):825-33.
5. McManus D P, Loukas A. Current status of vaccines for schistosomiasis. Clin Microbiol Rev 2008; 21(January (1)):225-42.
6. Siddiqui A A, Zhou Y, Podesta R B, Karcz S R, Tognon C E, Strejan G H, et al. Characterization of Ca(2+)-dependent neutral protease (calpain) from human blood flukes, *Schistosoma mansoni*. Biochim Biophys Acta 1993; 1181 (March (1)):37-44.
7. Karcz S R, Podesta R B, Siddiqui A A, Dekaban G A, Strejan G H, Clarke M W. Molecular cloning and sequence analysis of a calcium-activated neutral protease (calpain) from *Schistosoma mansoni*. Mol Biochem Parasitol 1991; 49(December (2)):333-6.
8. Silva E E, Clarke M W, Podesta R B. Characterization of a C3 receptor on the envelope of *Schistosoma mansoni*. J Immunol 1993; 151(December (12)):7057-66.
9. Young B W, Podesta R B. Complement and 5-HT increase phosphatidylcholine incorporation into the outer bilayers of *Schistosoma mansoni*. J Parasitol 1986; 72(October (5)): 802-3.
10. Van Hellemond J J, Retra K, Brouwers J F, et al. Functions of the tegument of schistosomes: clues from the proteome and lipidome. Int J Parasitol 2006; 36(May (6)):691-9.
11. Ahmad G, Torben W, Zhang W, Wyatt M, Siddiqui A A. Sm-p80 based DNA vaccine formulation induces potent protective immunity against *Schistosoma mansoni*. Parasite Immunol 2009; 31(March (3)):156-61.
12. Hota-Mitchell S, Siddiqui A A, Dekaban G A, Smith J, Tognon C, Podesta R B. Protection against *Schistosoma mansoni* infection with a recombinant baculovirus-expressed subunit of calpain. Vaccine 1997; 15(October (15)):1631-40.
13. Hota-Mitchell S, Clarke M W, Podesta R B, Dekaban G A. Recombinant vaccinia viruses and gene gun vectors expressing the large subunit of *Schistosoma mansoni* calpain used in a murine immunization-challenge model. Vaccine 1999; 17(March (11-12)):1338-54.
14. Siddiqui A A, Phillips T, Charest H, Podesta R B, Quinlin M L, Pinkston J R, et al. Enhancement of Sm-p80 (large subunit of calpain) induced protective immunity against *Schistosoma mansoni* through co-delivery of interleukin-2 and interleukin-12 in a DNA vaccine formulation. Vaccine 2003; 21(June (21-22)):2882-9.
15. Siddiqui A A, Pinkston J R, Quinlin M L, Kavikondala V, Rewers-Felkins K A, Phillips T, et al. Characterization of protective immunity induced against *Schistosoma mansoni* via DNA priming with the large subunit of calpain (Sm-p80) in the presence of genetic adjuvants. Parasite 2005; 12(March (1)):3-8.
16. Jankovic D, Aslund L, Oswald I P, Caspar P, Champion C, Pearce E, et al. Calpain is the target antigen of a Th1 clone that transfers protective immunity against *Schistosoma mansoni*. J Immunol 1996; 157(July (2)):806-14.
17. Ohta N, Kumagai T, Maruyama H, Yoshida A, He Y, Zhang R. Research on calpain of *Schistosoma japonicum* as a vaccine candidate. Parasitol Int 2004; 53(June (2)): 175-81.
18. Ridi R E, Tallima H. *Schistosoma mansoni* ex vivo lung-stage larvae excretory-secretory antigens as vaccine candidates against schistosomiasis. Vaccine 2009; 27(5):666-73.
19. Zhang R, Yoshida A, Kumagai T, Kawaguchi H, Maruyama H, Suzuki T, et al. Vaccination with calpain induces a Th1-biased protective immune response against *Schistosoma japonicum*. Infect Immun 2001; 69(January (1)):386-91.
20. Kennedy R C, Shearer M H, Hildebrand W. Nonhuman primate models to evaluate vaccine safety and immunogenicity. Vaccine 1997; 15(June (8)):903-8.
21. Siddiqui A A, Phillips T, Charest H, Podesta R B, Quinlin M L, Pinkston J R, et al. Induction of protective immunity against *Schistosoma mansoni* via DNA priming and boosting with the large subunit of calpain (Sm-p80): adjuvant effects of granulocyte-macrophage colony-stimulating factor and interleukin-4. Infect Immun 2003; 71(July (7)): 3844-51.
22. Siddiqui A A, Pinkston J R, Quinlin M L, Saeed Q, White G L, Shearer M H, et al. Characterization of the immune response to DNA vaccination strategies for schistosomiasis candidate antigen, Sm-p80 in the baboon. Vaccine 2005; 23(February (12)):1451-6.
23. Smithers S R, Terry R J. The infection of laboratory hosts with cercariae of *Schistosoma mansoni* and the recovery of the adult worms. Parasitology 1965; 55(November (4)): 695-700.
24. Damian R T, Greene N D, Fitzgerald K. Schistosomiasis mansoni in baboons. The effect of surgical transfer of adult *Schistosoma mansoni* upon subsequent challenge infection. Am J Trop Med Hyg 1972; 21(November (6)):951-8.
25. Cheever A W. Conditions affecting the accuracy of potassium hydroxide digestion techniques for counting *Schistosoma mansoni* eggs in tissues. Bull World Health Organ 1968; 39(2):328-31.
26. Shearer M H, Dark R D, Chodosh J, Kennedy R C. Comparison and characterization of immunoglobulin G subclasses among primate species. Clin Diagn Lab Immunol 1999; 6(November (6)):953-8.
27. Vereecken K, Naus C W, Polman K, Scott J T, Diop M, Gryseels B, et al. Associations between specific antibody responses and resistance to reinfection in a Senegalese population recently exposed to *Schistosoma mansoni*. TropMed Int Health 2007; 12(March (3)):431-44.
28. Acosta L P, Waine G, Aligui G D, Tiu W U, Olveda R M, McManus D P. Immune correlate study on human *Schistosoma japonicum* in a well-defined population in Leyte, Philippines. II. Cellular immune responses to *S. japonicum* recombinant and native antigens. Acta Trop 2002; 84(November (2)):137-49.
29. Olds G R. New insights into the observed age-specific resistance to reinfection with *Schistosoma japonicum*. Clin Infect Dis 2006; 42(June (12)):1699-701.
30. Hewitson J P, Hamblin P A, Mountford A P. Immunity induced by the radiation-attenuated schistosome vaccine. Parasite Immunol 2005; 27(July (7-8)):271-80.
31. Lightowlers M W. Cestode vaccines: origins, current status and future prospects. Parasitology 2006; 133(Suppl.): 527-42.
32. Vercruysse J, Schetters T P, Knox D P, Willadsen P, Claerebout E. Control of parasitic disease using vaccines: an answer to drug resistance? Rev Sci Tech 2007; 26(April (1)):105-15.
33. Kumagai T, Maruyama H, Hato M, Ohmae H, Osada Y, Kanazawa T, et al. *Schistosoma japonicum*: localization of calpain in the penetration glands and secretions of cercariae. Exp Parasitol 2005; 109(January (1)):53-7.
34. Damian R T, de la Rosa M A, Murfin D J, Rawlings C A, Weina P J, Xue Y P. Further development of the baboon as a model for acute schistosomiasis. Mem Inst Oswaldo Cruz 1992; 87(Suppl. 4):261-9.
35. Nyindo M, Farah I O. The baboon as a non-human primate model of human schistosome infection. Parasitol Today 1999; 15(December (12)):478-82.
36. Boulanger D, Reid G D, Sturrock R F, Wolowczuk I, Balloul J M, Grezel D, et al. Immunization of mice and baboons with the recombinant Sm28GST affects both worm viability and fecundity after experimental infection with *Schistosoma mansoni*. Parasite Immunol 1991; 13(September (5)): 473-90.
37. Kanamura H Y, Hancock K, Rodrigues V, Damian R T. *Schistosoma mansoni* heat shock protein 70 elicits an early humoral immune response in *S. mansoni* infected baboons. Mem Inst Oswaldo Cruz 2002; 97(July (5)):711-6.
38. Kariuki T M, Farah I O, Yole D S, Mwenda J M, Van Dam G J, Deelder A M, et al. Parameters of the attenuated schistosome vaccine evaluated in the olive baboon. Infect Immun 2004; 72(September (9)):5526-9.
39. Reid G D, Sturrock R F, Harrison R A, Tarara R P. *Schistosoma haematobium* in the baboon (*Papio anubis*): assessment of protection levels against either a single mass challenge or repeated trickle challenges after vaccination with irradiated schistosomula. J Helminthol 1995; 69(June (2)):139-47.
40. Soisson L A, Reid G D, Farah I O, Nyindo M, Strand M. Protective immunity in baboons vaccinated with a recombinant antigen or radiation attenuated cercariae of *Schistosoma mansoni* is antibody-dependent. J Immunol 1993; 151(November (9)):4782-9.
41. Yole D S, Pemberton R, Reid G D, Wilson R A. Protective immunity to *Schistosoma mansoni* induced in the olive baboon *Papio anubis* by the irradiated cercaria vaccine. Parasitology 1996; 112(January (Pt 1)):37-46.
42. Kariuki T M, Farah I O. Resistance to re-infection after exposure to normal and attenuated schistosome parasites in the baboon model. Parasite Immunol 2005; 27(July (7-8)): 281-8.
43. Stacy S, Pasquali A, Sexton V L, Cantwell A M, Kraig E, Dube P H. An age old paradigm challenged: old baboons generate vigorous humoral immune responses to LcrV, a plague antigen. J Immunol 2008; 181(July (1)):109-15.
44. Coulson P S, Kariuki T M. Schistosome vaccine testing: lessons from the baboon model. Mem Inst Oswaldo Cruz 2006; 101(September (Suppl. 1)): 369-72.
45. Wilson R A, Langermans J A, van Dam G J, Vervenne R A, Hall S L, Borges W C, et al. Elimination of *Schistosoma mansoni* adult worms by rhesus macaques: basis for a therapeutic vaccine? PLoS Negl Trop Dis 2008; 2(9):e290.
46. Ahmad G, Zhang W, Torben W, Damian R T, Wolf R F, White G L, Chavez-Suarez M, Kennedy R C, Siddiqui A A. Protective and antifecundity effects of Sm-p80-based DNA vaccine formulation against *Schistosoma mansoni* in a nonhuman primate model. Vaccine 27 (2009): 2830-2837.

We claim:

1. A method for preventing schistosomiasis, said method comprising the steps of:
   administering an effective dose of a vaccine comprising a single expression vector that comprises:
      a pcDNA3.1 expression vector;
      a full length cDNA of the large subunit of Schistosoma mansoni calpain (Sm-p80); and
      a flanking CpG oligonucleotide as an adjuvant,
   wherein the effective dose is an amount sufficient to provide worm reduction in the host, antifecundity effect, or protection against acute schistosomiasis.

2. The method of claim 1, wherein the vector is VR1020.

3. The method of claim 1, wherein the vaccine is administered with a primary immunization at week 0, a first boost at week 4, and a second boost at week 8.

4. The method of claim 1, wherein the vaccine is administered with a primary immunization at week 0, further comprising the steps of administering a first boost at week 4 comprising the vaccine and a Th1 response enhancer as adjuvant, and administering a second boost at week 8 comprising the vaccine and a Th1 response enhancher as adjuvant.

5. The method of claim 1, further comprising a Th1 response enhancer adjuvant.

6. The method of claim 5, wherein the Th1 response enhancer adjuvant comprises one or more CpG oligonucleotides.

7. The method of claim 5, wherein the adjuvant is immune modulator resiquimod (R848).

8. A schistosomiasis vaccine comprising:
   a full length cDNA of the large subunit of S. mansoni calpain (Sm-p80) and a flanking CpG oligonucleotide as an adjuvant cloned into a pcDNA3.1 expression vector.

9. The vaccine of claim 8, wherein the vector is VR1020.

10. The schistosomiasis vaccine of claim 8, further comprising a Th1 response enhancer adjuvant.

11. The schistosomiasis vaccine of claim 8, wherein the Th1 response enhancer adjuvant comprises a CpG oligonucleotide.

12. The vaccine of claim 10, wherein the adjuvant is immune modulator resiquimod (R848).

* * * * *